US009180196B2

(12) United States Patent
Anseth et al.

(10) Patent No.: US 9,180,196 B2
(45) Date of Patent: *Nov. 10, 2015

(54) PHOTODEGRADABLE GROUPS FOR TUNABLE POLYMERIC MATERIALS

(71) Applicant: The Regents of the University of Colorado, a Body Corporate, Boulder, CO (US)

(72) Inventors: Kristi S. Anseth, Boulder, CO (US); Andrea M. Kasko, Boulder, CO (US); Mark W. Tibbitt, Boulder, CO (US); April M. Kloxin, Newark, DE (US); Balaji Sridhar, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 94 days.

This patent is subject to a terminal disclaimer.

(21) Appl. No.: 13/725,674

(22) Filed: Dec. 21, 2012

(65) Prior Publication Data

US 2014/0031285 A1      Jan. 30, 2014

Related U.S. Application Data

(63) Continuation-in-part of application No. 11/374,471, filed on Mar. 13, 2006, now Pat. No. 8,343,710.

(60) Provisional application No. 60/660,945, filed on Mar. 11, 2005.

(51) Int. Cl.
| | |
|---|---|
| *C08F 20/34* | (2006.01) |
| *C08F 220/34* | (2006.01) |
| *C08G 75/00* | (2006.01) |
| *A61K 47/34* | (2006.01) |
| *A61K 38/38* | (2006.01) |
| *G03F 7/00* | (2006.01) |
| *A61K 41/00* | (2006.01) |
| *A61K 38/18* | (2006.01) |
| *A61K 38/36* | (2006.01) |

(52) U.S. Cl.
CPC ............ *A61K 47/34* (2013.01); *A61K 38/1841* (2013.01); *A61K 38/36* (2013.01); *A61K 38/385* (2013.01); *A61K 41/0042* (2013.01); *C08F 20/34* (2013.01); *C08F 220/34* (2013.01); *C08G 75/00* (2013.01); *G03F 7/0037* (2013.01)

(58) Field of Classification Search
CPC . A61K 47/24; A61K 41/0042; A61K 38/385; A61K 38/1841; A61K 38/36; C08F 220/34; C08F 20/34; C08G 72/00; G03F 7/0037
USPC .......... 430/281.1, 282.1, 283.1, 284.1, 285.1, 430/286.1, 287.1, 288.1; 522/173, 178, 522/181, 182; 568/584, 939
See application file for complete search history.

(56) References Cited

U.S. PATENT DOCUMENTS

| | | |
|---|---|---|
| 3,853,814 A | 12/1974 | Guillet |
| 3,860,538 A | 1/1975 | Guillet et al. |
| 3,903,064 A | 9/1975 | Isigami et al. |
| 3,963,491 A | 6/1976 | Marsh |
| 3,963,791 A | 6/1976 | Giuffre et al. |
| 4,013,572 A | 3/1977 | Marsh et al. |
| 4,028,480 A | 6/1977 | Le Brasseur |
| 4,176,145 A | 11/1979 | Guillet |
| 4,186,003 A | 1/1980 | Marsh et al. |

(Continued)

FOREIGN PATENT DOCUMENTS

| | | |
|---|---|---|
| EP | 0 392 759 | 10/1990 |
| EP | 0 426 436 A2 | 5/1991 |

(Continued)

OTHER PUBLICATIONS

Baldursodottir et al. (2003) "Riboflavion-Photosentitized Changes in Aqueous Solutions of Alginate. Rheological Studies," *Biomacromolecules* 4:429-436.
Furuta et al. (Feb. 1999) "Brominated 7-Hydroxycoumarin-4-ylmethyls: Photolabile Protecting Groups with Biologically Useful Cross-Sections for Two Photon Photolysis," *Proc. Nat. Acad. Sci. USA* 96:1193-1200.

(Continued)

*Primary Examiner* — Sanza McClendon
(74) *Attorney, Agent, or Firm* — Kilpatrick Townsend & Stockton LLP

(57) ABSTRACT

Here, we present a photodegradable microparticle system that can be employed to entrap and deliver bioactive proteins to cells during culture. By using a photosensitive delivery system, experimenters can achieve a wide variety of spatiotemporally regulated release profiles with a single microparticle formulation, thereby enabling one to probe many questions as to how protein presentation can be manipulated to regulate cell function. Photodegradable microparticles were synthesized via inverse suspension polymerization with a mean diameter of 22 μm, and degradation was demonstrated upon exposure to several irradiation conditions. The protein-loaded depots were incorporated into cell cultures and release of bioactive protein was quantified during the photodegradation process. This phototriggered release allowed for the delivery of TGF-β1 to stimulate PE25 cells and for the delivery of fluorescently labeled Annexin V to assay apoptotic 3T3 fibroblasts during culture. By incorporating these photoresponsive protein delivery depots into cell culture, new types of experiments are now possible to test hypotheses about how individual or multiple soluble factors might affect cell function when presented in a uniform, temporally varying, or gradient manner.

30 Claims, 10 Drawing Sheets

(56) References Cited

U.S. PATENT DOCUMENTS

| | | |
|---|---|---|
| 4,978,498 A | 12/1990 | Yoshihiro et al. |
| 5,164,420 A | 11/1992 | Dais |
| 5,194,527 A | 3/1993 | O'Brien et al. |
| 5,204,412 A | 4/1993 | Davidson et al. |
| 5,306,505 A | 4/1994 | Kuzuya et al. |
| 5,360,892 A | 11/1994 | Bonsignore et al. |
| 5,434,272 A | 7/1995 | Corrie et al. |
| 5,434,277 A | 7/1995 | Hwu et al. |
| 5,489,678 A | 2/1996 | Fodor et al. |
| 5,626,863 A | 5/1997 | Hubbell et al. |
| 5,635,608 A | 6/1997 | Haugland et al. |
| 5,739,386 A | 4/1998 | Holmes |
| 5,763,599 A | 6/1998 | Pfleiderer et al. |
| 5,773,308 A | 6/1998 | Conrad et al. |
| 5,981,207 A | 11/1999 | Burbaum et al. |
| 5,986,043 A | 11/1999 | Hubbell et al. |
| 6,022,963 A | 2/2000 | McGall et al. |
| 6,147,205 A | 11/2000 | McGall et al. |
| 6,306,922 B1 | 10/2001 | Hubbell et al. |
| 6,322,970 B1 | 11/2001 | Little et al. |
| 6,342,349 B1 | 1/2002 | Virtanen |
| 6,566,515 B1 | 5/2003 | McGall et al. |
| 6,602,975 B2 | 8/2003 | Hubbell et al. |
| 6,703,037 B1 | 3/2004 | Hubbell et al. |
| 6,738,661 B1 | 5/2004 | Nyhart, Jr. |
| 6,750,335 B2 | 6/2004 | Pfleiderer et al. |
| 6,756,492 B1 | 6/2004 | Beier et al. |
| 7,541,193 B2 | 6/2009 | Nguyen et al. |
| 7,544,721 B2 | 6/2009 | Gaud et al. |
| 2003/0215395 A1 | 11/2003 | Yu et al. |
| 2006/0194145 A1 | 8/2006 | Irvine et al. |

FOREIGN PATENT DOCUMENTS

| | | |
|---|---|---|
| EP | 0 426 436 A3 | 1/1992 |
| WO | 90/12049 | 10/1990 |
| WO | 94/10128 | 5/1994 |
| WO | 03/097107 | 11/2003 |
| WO | 2004/087777 | 10/2004 |

OTHER PUBLICATIONS

Holmes et al. (1995) "Reagents for Combinatorial Organic Synthesis: Development of a New O-Nitrobenzyl Photolabile Linker for Solid Phase Synthesis," *J. Org. Chem.* 60:2318-2319.

Johnson et al. (2007) "Synthesis of Photocleavable Linear Macromonomers by ATRP and Star Macromonomers by a Tandem ATRP-Click Reaction: Precursors to Photodegradable Model Networks," *Macromolecules* 40:3589-3598.

Kjoniksen et al. (2004) "Characterization of Riboflavin-Photoseneitized Changes in Aqueous Solutions of Alginate. Rheological Studies," *Macromol. Biosci.* 4(2):76-83.

Kolb et al. (2003) "The Growing Impact of Click Chemistry in Drug Discovery," *Drug Discov. Today* 8(24):1128-1137.

Lei et al. (Oct. 12, 2004) "High-Resolution Technique for Fabricating Environmentally Sensitive Hydrogel Microstructures," *Langmuir* 20(21):8947-8951.

Luo et al. (Apr. 2004) "A Photolabile Hydrogel for Guided Three-Dimensional Cell Growth and Migration," *Nat. Mater.* 3:249-253.

Nuttleman et al. (2005) "Dexamethasone-Functionalized Gels Induce Osteogenic Differentiation of Encapsulated hMSCs," *J. Biomed. Mater. Res. A* 76A: 183-195.

Ruhland et al. (1996) "Solid-Supported Combinatorial Synthesis of Structurally Diverse Beta-Lactams," *J. Am. Chem. Soc.* 118:253-254.

Wang et al. (2003) "Bioconjugation by Copper(I)-Catalyzed Azide-Aikyne [3+2] Cycloaddition," *J. Am. Chem. Soc.* 125:3192-3193.

Wilcox et al. (1990) "Synthesis of Photolabile "Precursors" of Amino Acid Neurotransmitters," *J. Org. Chem.* 55:1585-1589.

Yui et al. (1993) "Photo-Responsive Degradation of Heterogeneous Hydrogels Comprising Cross-Linked Hyaluronic-Acid and Lipid Microspheres for Temporal Drug- Delivery," *J. Controlled Release* 26(2):141-145.

Zhao et al. (2004) "New Caged Coumarin Fluorophores with Extraordinary Uncaging Cross Sections Suitable for Biological Imaging Applications," *J. Am. Chem. Soc.* 126:4653-4663.

PHOTODEGRADABLE GROUPS FOR TUNABLE POLYMERIC MATERIALS

CROSS-REFERENCE TO RELATED APPLICATIONS

This application is a continuation-in-part application of U.S. patent application Ser. No. 11/374,471, filed Mar. 13, 2006, now U.S. Pat. No. 8,343,710, which application claims priority from U.S. provisional application No. 60/660,945, filed Mar. 11, 2005, which are all incorporated by reference.

BACKGROUND OF THE INVENTION

Materials and biomaterials with tunable properties are useful in numerous applications ranging from tissue engineering and drug delivery to materials processing and recycling. A critical aspect of designing biomaterial carriers for cell and/or drug delivery is tuning and controlling the material's degradation behavior.

Current degradation technology uses hydrolysis and/or enzymatic degradation, which are sustained processes that offer minimal spatial or temporal control. Most synthetic biomaterials degrade via hydrolysis, which can occur throughout the bulk or only at the surface of a biomaterial and leads to a sustained and non-instantaneous mass loss, which may be undesirable. Current photopolymerization and photodegradation techniques require the use of a photosensitizer, and often have no spatial control.

There is a need for an improved degradation process that allows for spatial and temporal control of degradation.

SUMMARY OF THE INVENTION

Provided is a method that provides both spatial and temporal control of the degradation process using mono- and multifunctional macromolecular monomers ("macromers") that degrade via single- and multi-photon photolysis mechanisms over a broad range of wavelengths. The macromers can form or be incorporated into networks via covalent, non-covalent and/or ionic interactions. These networks can controllably degrade both spatially and temporally.

More specifically, provided is a photodegradable macromer, comprising: (a) a photodegradable group; (b) a backbone structure comprising one or more repeating units that may be the same or different, which backbone structure is attached to the photodegradable group directly or through a linker; (c) one or more reactive end groups at one or more ends of the macromer; and optionally, (d) one or more therapeutic agents; and optionally (e) one or more caged groups.

Also provided are polymers and networks incorporating macromers of the invention and optionally other substituents such as other polymeric structures.

Also provided is a method of controlled degradation of a polymer comprising: providing a photodegradable polymer as described herein and exposing the photodegradable polymer to photoradiation of the appropriate wavelength and energy to cause one or more of the photodegradable groups to photodegrade.

As used herein, "photodegradable group" is a group that breaks one or more bonds in response to exposure to radiation of the appropriate wavelength and energy. The appropriate wavelength and energy is easily determinable by one of ordinary skill in the art without undue experimentation such as by the use of an absorbance spectrum to determine what wavelength(s) will cause photodegradation. The degradation of the photodegradable group does not need a photosensitizer, although a photosensitizer may be used if desired. The use of the invention with a photosensitizer is easily performed by one of ordinary skill in the art without undue experimentation. Single- or multi-photon photolysis can be used to photodegrade the photodegradable group. A broad range of wavelengths may be used for photodegradation, for example, those wavelengths in the ultraviolet spectrum, visible and infrared spectrum (between about 180 nm and 1.5 µm, for example) and all individual values and ranges therein, including UV-A (between about 320 and about 400 nm); UV-B (between about 280 and about 320 nm); and UV-C (between about 200 and about 280 nm). Other useful ranges include the radiation from visible, near-IR and IR lasers (about 500 nm to about 1.5 µm). All individual wavelengths and all intermediate ranges therein are intended to be included in this disclosure as if they were each listed separately.

Examples of photodegradable groups include those groups having the structure:

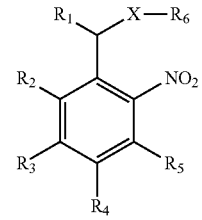

where X is O, N or S;

$R_1$ is selected from the group consisting of: hydrogen, straight-chain or branched $C_1$-$C_{10}$ alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;

$R_2$-$R_6$ are independently selected from the group consisting of: hydrogen; one or more polymerizable groups, one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms; one or more R groups can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO—R'; —N(R')$_2$; —CO—N(R')$_2$; —NR'—CO—OR'; —SR'; —SOR'; —$SO_2$—R'; —$SO_3R'$; —$SO_2N(R')_2$; —P(R')$_2$; —$OPO_3(R')_2$; and —Si(R')$_3$ wherein each R', independent of other R' in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or —NH group; an optionally substituted aromatic group, two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups; and any of the R groups may be linked to the backbone structure, reactive end group or other groups directly or using a linker.

One class of photodegradable groups has the formula:

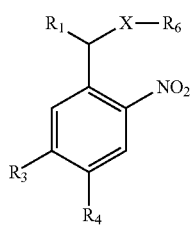

wherein $R_1$ is hydrogen or a $C_1$-$C_3$ alkyl group; $R_3$ and $R_4$ are independently hydrogen or a $C_1$-$C_{10}$ straight chain or branched alkyl group wherein one or more carbon atoms in the chain may be replaced with oxygen and R6 comprises a backbone structure, a reactive end group, a therapeutic agent or a caged group. In one class of macromers of the invention, a reactive end group is an acrylate group, and the backbone comprises poly(ethylene glycol).

One class of photodegradable groups contains a nitro group ortho to an ester functionality on an aromatic ring structure. Other examples of photodegradable groups are known in the art, including those photodegradable groups described in WO 94/10128; 5,489,678; 5,763,599; 6,022,963; 6,147,205; 6,566,515; 6,756,492; 6,750,335; Furuta, et al. Proc. Natl. Acad. Sci. USA 96: 1193-1200 (February 1999); Holmes, et al. J. Org. Chem. 60: 2318-2319 (1995); Wilcox, et al. J. Org. Chem. 55: 1585-1589 (1990); Zhao, et al., J. Am. Chem. Soc. 126: 4653-4663 (2004), which references are incorporated by reference.

As used herein, a "macromer" is a group comprising one or more repeating units and one or more reactive end groups that allow reaction with another group.

The "backbone structure" comprises any repeating unit into which a photodegradable group can be attached. There are many repeating units known in the art. All repeating units that function in the macromers and polymers of the invention are intended to be included in this disclosure, even if not specifically mentioned. Some examples of useful repeating units include poly(ethylene glycol), poly(ethylene oxide), poly(vinyl alcohol), poly(vinylpyrrolidone), poly(ethyloxozoline), poly(ethylene oxide)/poly(propyleneoxide) block copolymers, polysaccharides, poly(hydroxylethylmethacrylates), poly(urethanes), poly(hydroxyethylacrylates), collagen, poly(ester)s, poly α-hydroxyesters, carbohydrates, proteins, poly(oxazoline), polyamino acids, poly(lactides), poly(styrenes), poly(acrylates), poly(methacrylates), poly(vinylethers), polyethylenes, poly(ethylene imine)s, polyesters, poly(urethane)s, and polypropylenes or any other polymer known in the art, and combinations thereof. Some backbones that are particularly useful for lithographic applications include poly(styrene), poly(acrylate), poly(methacrylate), poly(vinyl ether). The backbone can contain two or more different repeating units in any sequence, including random, gradient, alternating or block. The repeating units may be amphiphilic with respect to each other, the photodegradable group, the reactive end group and any other group in the macromer.

"Reactive end groups" include those groups that are polymerizable by cationic, anionic, coordination, free-radical, condensation and/or other reactions as known in the art such as a pseudo-Michael addition. The reactive end groups may also form polymers through ionic interactions, self-assembly or non-covalent interactions, as known in the art. There are many reactive end groups known in the art. All reactive end groups that function in the macromers and polymers of the invention are intended to be included in this disclosure, even if not specifically mentioned. Some examples of reactive end groups include: acrylate, methacrylate, styrene, allyl ether, vinyl ether, isocyanate, cyanoacrylate, triazide, phosphazine, imine, oxazoline, propylene sulfide, groups polymerizable using condensation reactions as known in the art, alkene, alkyne, "click" chemistry, carboxylic acid, epoxide, isocyanate, and other polymerizable groups known in the art (such as those produced by condensation of carboxylic acids with alcohols or amines to form polyesters or polyamides). Polymerization using reactive end groups is well-known in the art. Click chemistry (developed in the Sharpless group at The Scripps Research Institute) utilizes the copper (I) triazole formation from alkynes and azides, a highly efficient reaction (Wang, Q.; Chan, T. R.; Hilgraf, R.; Fokin, V. V.; Sharpless, K. B.; Finn, M. G. "Bioconjugation by Copper(I)-Catalyzed Azide-Alkyne [3+2] Cycloaddition", J. Am. Chem. Soc. 2003, 125, 3192). There is growing interest in "click" chemistry in many applications; the triazole products can associate with biological agents through dipole interactions and hydrogen bonding (Kolb, H. C.; Sharpless, K. B. "The Growing Impact of Click Chemistry in Drug Discovery" Drug Discov. Today 2003, 8(24), 1128-1137), As used herein, "therapeutic agent" includes those groups that cause a measurable physiological response in a mammal. The mammal may be human or non-human. Therapeutic agents are known in the art. All categories and specific therapeutic agents are intended to be included in this disclosure, even if not specifically mentioned. Therapeutic agents include enzymes, antibiotics, anesthetics, antibodies, growth factors, proteins, hormones, anti-inflammatories, analgesics, cardiac agents, and psychotropics.

As used herein, "caged groups" include those groups which may be activated upon photodegradation to elicit a fluorescent and/or chromagenic response, or a response that is detectable by other conventional analytical techniques. Caged groups can be attached to the photodegradable group, the end group, the backbone, or any other portion of the macromer. In one embodiment, caged groups are activated (have a different fluorescence or absorbance than when caged) upon photocleavage. This allows tracking of the progress of the photodegradation reaction. Fluorescein, bromohydroxycoumarin, fluorescent dyes and groups known in the art to be susceptible to two-photon photolysis are some useful caged groups, although there are other useful caged groups that are known in the art and that are intended to be included in this disclosure.

Any or all of the groups of the macromers of the invention can be attached to each other directly or through a linker to any other group in any desired order. Linkers are known in the art and include such groups as alkyl chains which may be optionally substituted with heteroatoms such as oxygen, carbonyl groups, aldehyde groups, ketone groups, halogens, nitro groups, amide groups, and combinations thereof, as well as any group that does not prevent the desired reaction from occurring.

The macromers of the invention may be copolymerized with other monomers, macromomers or reactive compounds. The macromers of the invention may be grafted on or reacted with surfaces, such as biological implants or surfaces coated with a biocompatible substance. In one embodiment of the invention, the macromers and polymers of the invention are formed and/or degraded in the presence of any biologically compatible material, such as proteins, carbohydrates, nucleic acids, organic and inorganic biologically active materials, tissues and tissue aggregates.

DETAILED DESCRIPTION OF THE INVENTION

The following non-limiting description is intended to further illustrate some embodiments of the invention.

Figure 1:
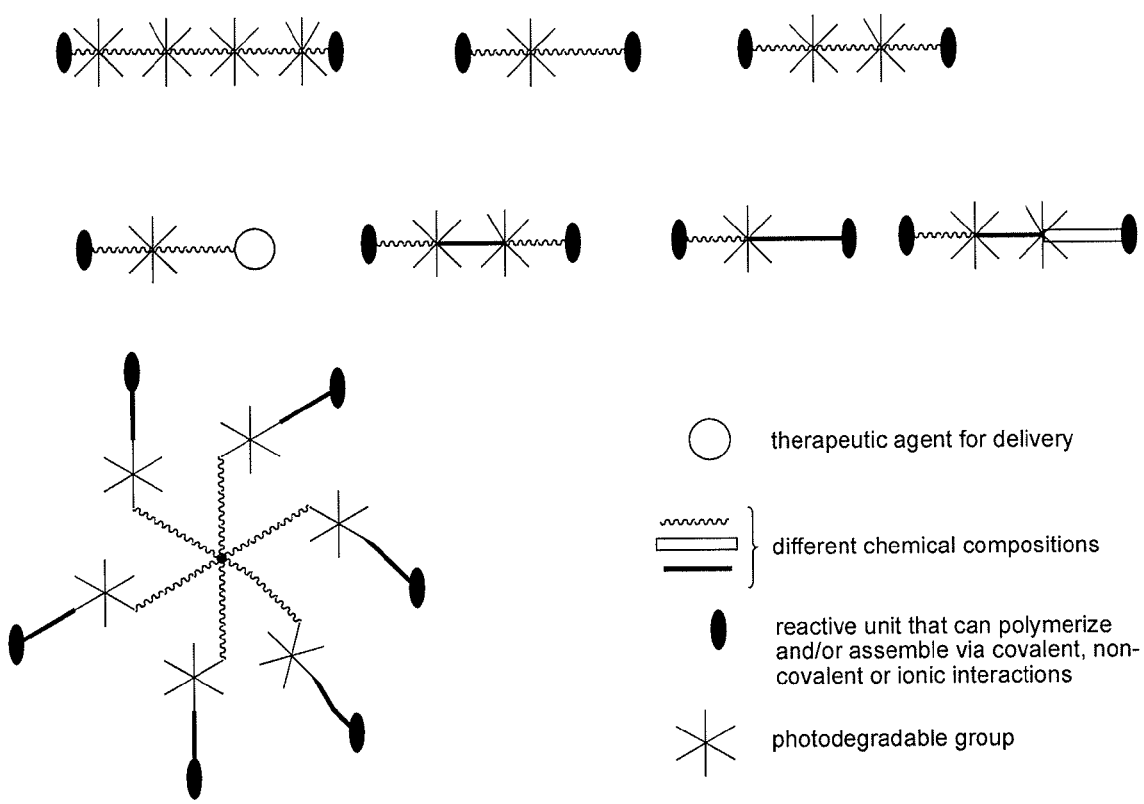
FIG. 1 shows some different examples of structures of the invention.

FIG. 1 shows some exemplary structures into which photodegradable groups can be incorporated according to the invention. Photodegradable groups can be incorporated into macromers, block copolymers, and linear and branched polymers, for example. They can be incorporated between a reactive end group, such as an olefin, and a therapeutic agent, for incorporation into a tissue scaffold to provide spatial and temporal control over the release of the agent. Photodegradable groups can be incorporated into linear structures and crosslinked structures to allow rapid and precise degradation of higher molecular weight materials. The macromers can form or be incorporated into networks via covalent, non-covalent and/or ionic interactions, as known in the art. These networks can be used for 3-D photolithography via single and multi-photon photolysis. Thin films of reacted macromers can be cast and then degraded for 2-D lithography. Incorporation of a chromagenic or fluorescent group (caged group) into the photodegradable linkage that is activated upon degradation allows for 2-D and 3-D imaging. The chromagenic or fluorescent group can be detected using any available technique.

The macromers can be amphiphilic, incorporating both hydrophobic and hydrophilic segments, or can be hydrophilic or hydrophobic. The macromers can be linear or branched, and can form linear, branched or crosslinked networks which are then photodegradable. These macromers can be incorporated or grafted onto surfaces to impart biocompatibility. The polymers and polymer networks formed from these macromers can, for example, undergo bulk degradation, surface degradation, gradient degradation and/or focused degradation that is spatially controllable. Multiple photodegradable groups which degrade at different wavelengths with or without a photosensitizer allows for multistage degradation, including surface and bulk patterning and spatial control over release of multiple groups. This can be used to control the timing and spatial release of therapeutics in different parts of the body, for example. The compositions of the invention can be combined with groups that undergo existing methods of degradation, such as hydrolysis or enzymatic degradation.

Incorporation of different photodegradable groups that photolyze at different wavelengths in one macromer or different macromers that are incorporated into a network allows a broad range of wavelengths to be used for photodegradation (such as those wavelengths≥300 nm (including light around 365 nm) but preferably in the longwave ultra-violet to visible light region for biological applications (because shorter wavelengths such as 280 nm cause mutations, damage and/or cell death) and intensities, and allows for multi-stage degradation where the degradation is temporally controlled by the timing of the application of the appropriate cleaving photoradiation for each different photodegradable group, dual degradation of different photodegradable groups by the simultaneous application of different cleaving photoradiation for each photodegradable group and/or release of desired substances. The degradation of one photodegradable group at one wavelength can be simultaneous with or at a different time than the degradation of another photodegradable group at a different wavelength by application of the appropriate wavelength.

Figure 2:
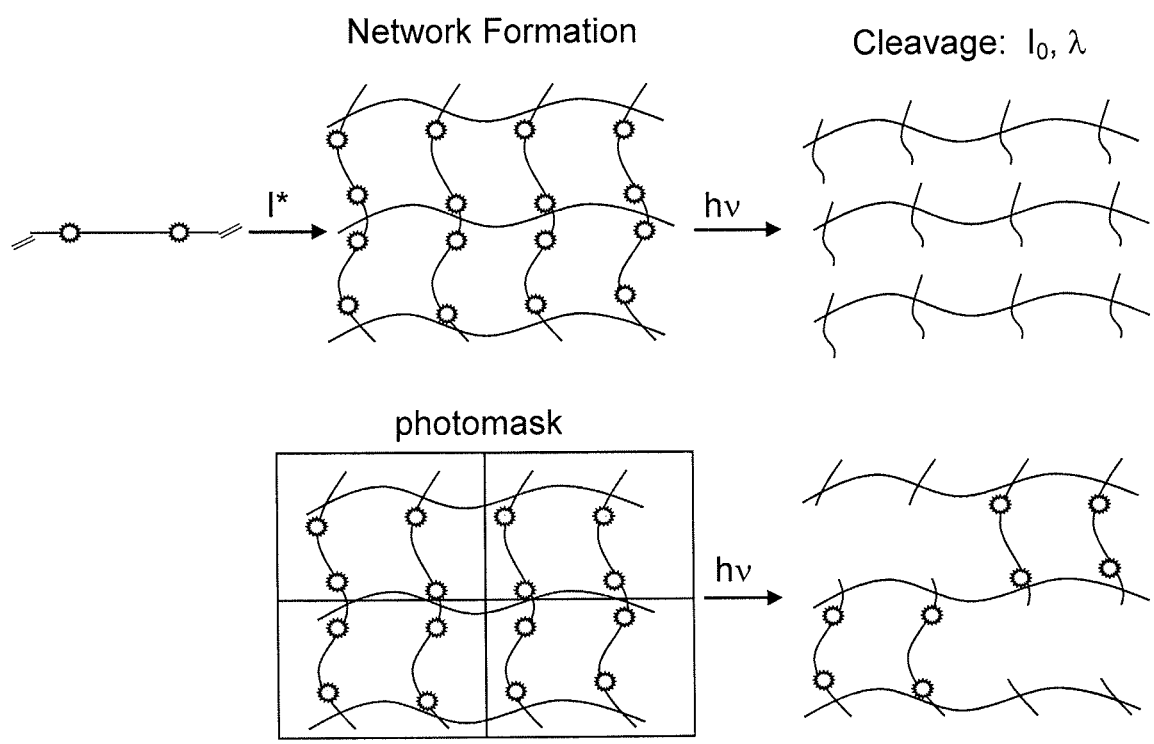
FIG. 2 shows a general description of the formation and cleavage of networks of macromers of the invention.

FIG. 2 shows one general description of the formation and cleavage of networks of macromers of the invention. A network is formed by the reaction of multiple photodegradable macromers with reactive end groups. Upon application of the appropriate wavelength and intensity of light, the photodegradable groups cleave (top of FIG. 2). Portions of the network can be masked using any material that the light does not penetrate, such as foil, a transparency film with printed black areas in a desired arrangement, or other masking materials known in the art, allowing the desired patterning of cleaved groups and uncleaved groups (bottom of FIG. 2). Sequential photodegradation of unmasked portions and masked portions then occurs by application of the appropriate wavelength.

Figure 3:
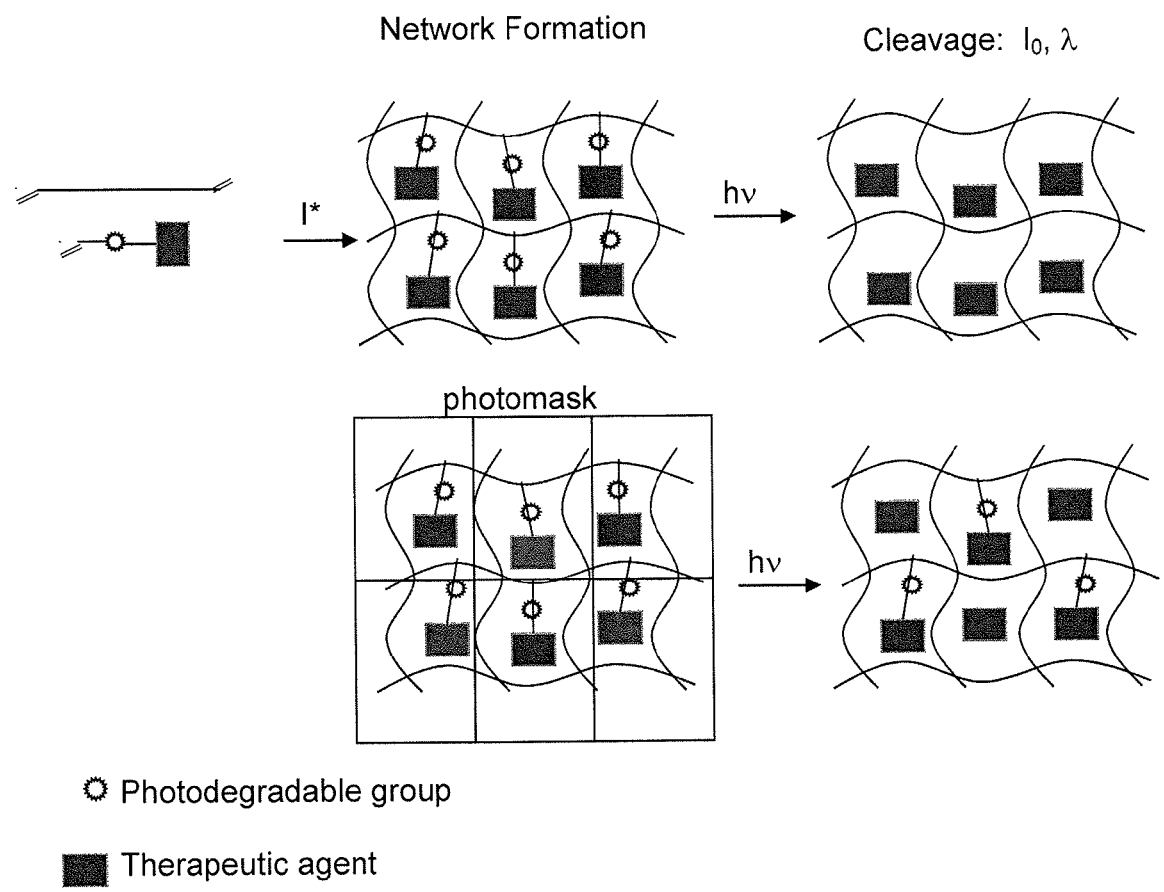
FIG. 3 shows a general description of the release of a therapeutic agent.

FIG. 3 shows one application of the invention using a therapeutic agent. As in FIG. 2, a network of photodegradable groups having therapeutic agents attached thereto is formed. As shown in FIG. 3, the network can be formed using different precursors, some having photodegradable groups with optional therapeutic agents which may be the same or different, and some not having photodegradable groups, allowing for the desired network composition. Upon application of light having the appropriate intensity and wavelength, the photodegradable groups cleave. Different photodegradable groups can be incorporated into the network to allow for degradation of different photodegradable groups with different light wavelengths. As shown in the bottom of FIG. 3, using a photomask, some of the photodegradable groups can be allowed to cleave upon the initial application of light and others can remain uncleaved. This allows the release of a portion of the therapeutic agent at one time and allows the release of a different portion of the therapeutic agent at a different time. Various combinations of therapeutic agents, caged groups, photodegradable groups, masks and other components can be used to provide the desired release profile by one of ordinary skill in the art without undue experimentation using the knowledge in the art and provided herein.

In one embodiment, the present invention provides a photodegradable composition comprising a photodegradable group having the formula:

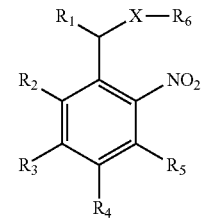

where X is O, N or S;

$R_1$ is selected from the group consisting of: hydrogen, straight-chain or branched $C_1$-$C_{10}$ alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;

one of the others of $R_2$, $R_3$, $R_4$, $R_5$ and $R_6$ is a backbone structure comprising one or more repeating units: poly (ethylene glycol), poly(ethylene oxide), poly(vinyl alcohol), poly(vinylpyrrolidone), poly(styrene), poly(acrylate), poly(methacrylates), poly(vinylethers), poly (urethane)s, polypropylene, polyester and polyethylene, —O—$CH_2$—$CH_2C(O)NH$—$(CH_2CH_2O)_n$—NH—C(O) $CH_2$—$CH_2$—O—, wherein n is 1-100 such as 1-75, or 1-50, or 1-25 or 1-10, or 1-5 or 1, 2, 3, or 4;

the others of $R_2$, $R_3$, $R_4$, $R_5$ and $R_6$ are each independently selected from the group consisting of: hydrogen; one or more polymerizable groups, one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms;

one or more R groups can be optionally substituted with one or more suibstituent groups selected from halogens; nitro groups; cyano groups; isocyano groups; thiocyano groups; isothiocyano groups; azide groups; —SO₂ groups; —OSO₃H groups; one or more optionally substituted straight-chain, branched or cyclic alkyl, alkenyl or alkynyl groups; OR'; —CO—OR'; —O—CO—R'; —N(R')₂; —CO—N(R')₂; —NR'—CO—OR'; —SR'; —SOR'; —SO₂—R'; —SO₃R'; —SO₂N(R1)₂; —P(R')₂; —OPO₃(R')₂; and —Si(R')₃, wherein each R', independent of other R' in the substituent group can be a hydrogen, an optionally substituted straight-chain, branched or cyclic alkyl, alkenyl or alkynyl group wherein one or more C, CH or CH₂ groups therein can be replaced with an O atom, N atom, S atom or —NH group; an optionally substituted aromatic group, two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —SO₂ groups; —OSO₃H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups; wherein at least one of $R_2$, $R_3$, $R_4$, $R_5$ and $R_6$ comprises a reactive end group.

In certain embodiments, the photodegradable composition has the structure wherein one of the others of $R_2$, $R_3$, $R_4$, and $R_5$ is a backbone structure comprising one or more repeating units; and the others of $R_2$, $R_3$, $R_4$, and $R_5$ are each independently selected from the group consisting of: hydrogen; one or more polymerizable groups, one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or CH₂ moiety can be replaced with an oxygen atom, a nitrogen atom, an NR' group, or a S atom; and an optionally substituted aromatic or non-aromatic ring structure.

In certain embodiments, the photodegradable group has the structure:

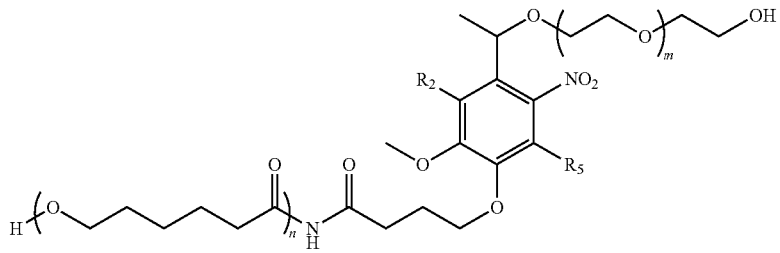

wherein m is an integer from 1-100, such as 1-75, or 1-50, or 1-25 or 1-10; and wherein n is an integer from 1-100 such as 1-75, or 1-50, or 1-25 or 1-10 or 1, 2, 3, 4, 5, 6, 7, 8, or 9.

In another aspect, the photodegradable group has the structure:

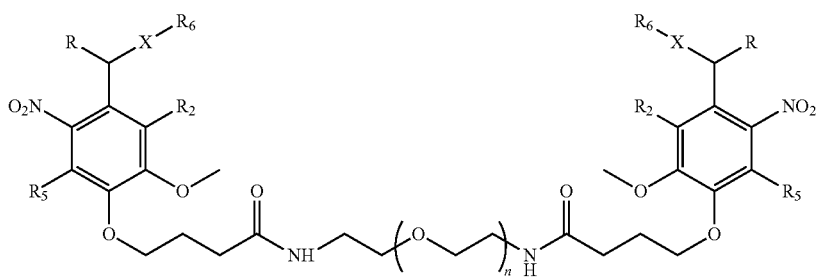

wherein n is an integer from 1-1000 such as 1-900, or 1-800, or 1-700, or 1-600, or 1-500, or 1-400, or 1-300, or 1-200, or 1-100, 1-75, or 1-50, or 1-25 or 1-10 or 1, 2, 3, 4, 5, 6, 7, 8, or 9. In certain instances, PEG5000 or PEG6000 is used. For PEGdiPDA, the range of n reflects a higher molecular weight range to include various PEG starting materials from PEG1000 to PEG6000.

In other aspects, the photodegradable group has the structure:

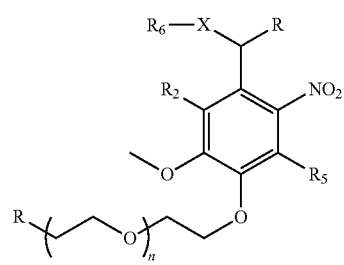

wherein n is an integer from 1-100 such as 1-75, or 1-50, or 1-25 or 1-10 or 1, 2, 3, 4, 5, 6, 7, 8, or 9.

In another aspect, the photodegradable group has the structure wherein X—R$_6$ is a member of the group consisting of

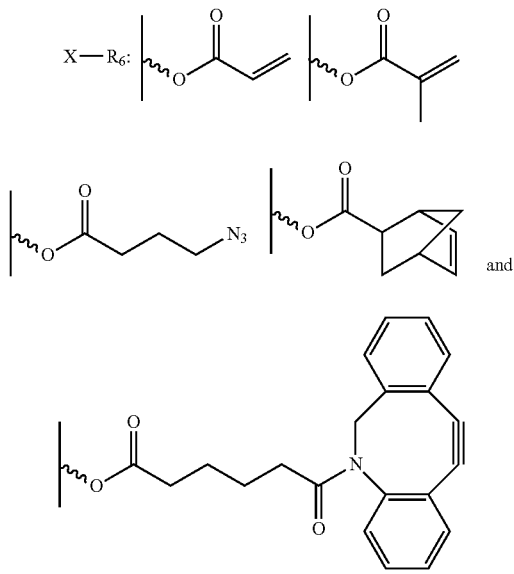

and

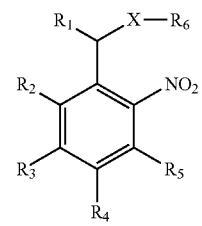

In certain aspects, the photodegradable group or macromer is poly(ethylene glycol)di-photodegrable-acrylate (PEG-diPDA). In other aspects, the photodegradable group is reacted with poly(ethylene glycol)tetrathiol (PEG$_4$SH). In some aspects, the photodegradable composition is a step-growth network.

In certain aspects, the photodegradable composition is a member selected from the group consisting of a microparticle, a nanoparticle, and a thin film. In certain aspects, the composition comprises an entrapped biomolecule, which biomolecule is optionally releasable upon photodegradation of the composition.

In certain aspects, the photodegradable composition is photodegraded with light irradiation at between 200 nm to 500 nm, or at 365 nm or 400-500 nm or at between 390 nm to 850 nm or even at 740 nm.

In certain aspects, the photodegradable composition comprises an entrapped biomolecule, which is a member selected from the group consisting of a protein, a peptide, an enzyme, an enzyme substrate, a vaccine, a hormone, an antibody, an antibody fragment, an antigen, a hapten, an avidin, a streptavidin, a carbohydrate, an oligosaccharide, a polysaccharide, a nucleic acid, a fragment of DNA, a fragment of RNA and a biological therapeutic.

In certain aspects, the entrapped biomolecule is a vaccine, wherein the vaccine is a vaccine against a viral disease or a bacterial disease. In certain aspects, the viral caused disease is selected from the group consisting of rabies, Hepatitis A, Hepatitis B, cervical cancer, genital warts, anogenital cancers, influenza, Japanese encephalitis, measles, mumps, rubella, poliomyelitis, rotaviral gastroenteritis, smallpox, chickenpox, shingles, and Yellow fever. In other aspects, the bacteria caused disease is selected from the group consisting of Anthrax, Whooping cough, Tetanus, Diphtheria, Q fever, Epiglottitis, meningitis, pneumonia, Tuberculosis, Meningococcal meningitis, Typhoid, fever, Pneumococcal pneumonia and Cholera.

In another embodiment, the present invention provides a method for making a photodegradable composition, the method comprising: copolymerizing a photodegradable group having the formula:

where X is O, N or S;
R$_1$ is selected from the group consisting of: hydrogen, straight-chain or branched C$_1$-C$_{10}$ alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;
one of the others of R$_2$, R$_3$, R$_4$, R$_5$ and R$_6$ is a backbone structure comprising one or more repeating units: poly(ethylene glycol), poly(ethylene oxide), poly(vinyl alcohol), poly(vinylpyrrolidone), poly(styrene), poly(acrylate), poly(methacrylates), poly(vinylethers), poly(urethane)s, polypropylene, polyester and polyethylene, —O—CH$_2$—CH$_2$C(O)NH—(CH$_2$CH$_2$O)$_n$—NH—C(O)CH$_2$—CH$_2$—O—, wherein n is 1-100 such as 1-75, or 1-50, or 1-25 or 1-10, or 1-5 or 1, 2, 3, or 4;
the others of R$_2$, R$_3$, R$_4$, R$_5$ and R$_6$ are each independently selected from the group consisting of: hydrogen; one or more polymerizable groups, one or more reactive end groups; straight chain, branched or cyclic C$_1$-C$_{20}$ alkyl, alkenyl, alkynyl groups in which one or more of the carbon atoms are optionally substituted with non-hydrogen substituents and wherein one or more C, CH or CH$_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms;
one or more R groups can be optionally substituted with one or more substituent groups selected from halogens; nitro groups; cyano groups; isocyano groups; thiocyano groups; isothiocyano groups; azide groups; —SO$_2$ groups; —OSO$_3$H groups; one or more optionally substituted straight-chain, branched or cyclic alkyl, alkenyl or alkynyl groups; OR'; —CO—OR'; —O—CO—R'; —N(R')$_2$; —CO—N(R')$_2$; —NR'—CO—OR'; —SR'; —SOR'; —SO$_2$—R'; —SO$_3$R'; —SO$_2$N(R1)$_2$; —P(R')$_2$; —OPO$_3$(R')$_2$; and —Si(R')$_3$, wherein each R', independent of other R' in the substituent group can be a hydrogen, an optionally substituted straight-chain, branched or cyclic alkyl, alkenyl or alkynyl group wherein one or more C, CH or CH$_2$ groups therein can be replaced with an O atom, N atom, S atom or —NH group; an optionally substituted aromatic group, two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —SO$_2$ groups; —OSO$_3$H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups; wherein at least one of R$_2$, R$_3$, R$_4$, R$_5$ and R$_6$ comprises a reactive end group, with a member selected from the group consisting of a monomer, a macromer or other reactive compound, such as PEG4SH.

SYNTHESIS EXAMPLES

Techniques. All reactions were performed under an argon atmosphere using a Schlenk line unless noted otherwise. $^1$H NMR spectra ($\delta$, ppm) were recorded on either a Varian Inova 400 (400 MHz) spectrometer. All spectra were recorded in CDCl$_3$ with tetramethylsilane (TMS) as an internal standard unless noted otherwise.

A general synthetic route to form photodegradable groups is shown in Scheme 1:

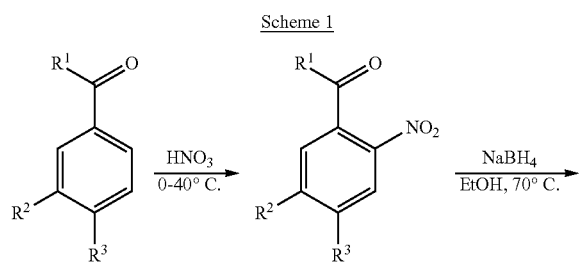

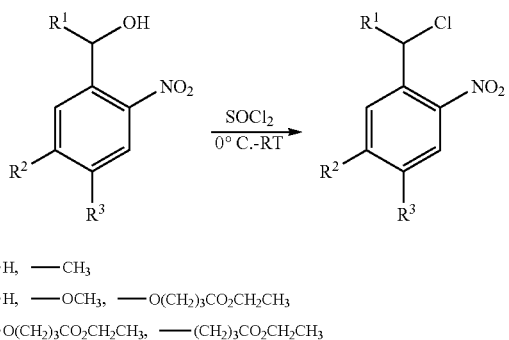

R$^1$= —H, —CH$_3$
R$^2$= —H, —OCH$_3$, —O(CH$_2$)$_3$CO$_2$CH$_2$CH$_3$
R$^3$= —O(CH$_2$)$_3$CO$_2$CH$_2$CH$_3$, —(CH$_2$)$_3$CO$_2$CH$_2$CH$_3$

The structures can be functionalized with reactive end groups using methods known in the art and described herein. In several of the schemes and compounds shown herein, the backbone group is shown in parenthesis without a number of repeating units specified. This structural information indicates the number of repeating units may be as many or as few as desired, as long as the structure functions in the desired way. As known in the art, compounds can be synthesized in different ways, as exemplified below.

Synthesis of the photodegradable group, poly(ethylene glycol)monoacrylate-4-(2-methoxy-5-nitro-4-(2-bromoethyl)phenoxy butanoate, is shown in Scheme 2. Acetovanillone was esterified with ethyl 4-bromobutyrate, and the resulting keto-ester converted to the oxime using hydroxylamine hydrochloride in pyridine. The oxime was then reduced to the amine using zinc in acetic acid, and the resulting amine protected with trifluoroacetic anhydride to yield ethyl 4-(2-methoxy-4-(1-trifluoroacetamidoethyl)phenoxy) butanoate. After nitration with nitric acid, the trifluoroacetamide group was removed under basic conditions. Ethyl 4-(2-methoxy-4-(2-aminoethyl)phenoxy) butanoate was converted to the bromide via diazotization using sodium nitrite in hydrobromic acid, while the ethyl ester was simultaneously cleaved, to yield 4-(2-methoxy-4-(2-bromoethyl) phenoxy)butanoic acid. This acid is converted to the acid chloride using thionyl chloride and used to esterify poly(ethylene glycol)monoacrylate.

In this example, the backbone is poly(ethylene glycol) and the reactive end group is acrylate. The bromide/chloride group allows for substitution reactions known in the art to make ethers and amides (and also thioesters).

Scheme 2. Synthesis of poly(ethylene glycol) monoacrylate-4-(2-methoxy-5-nitro-4-(2-bromoethyl)phenoxy butanoate).

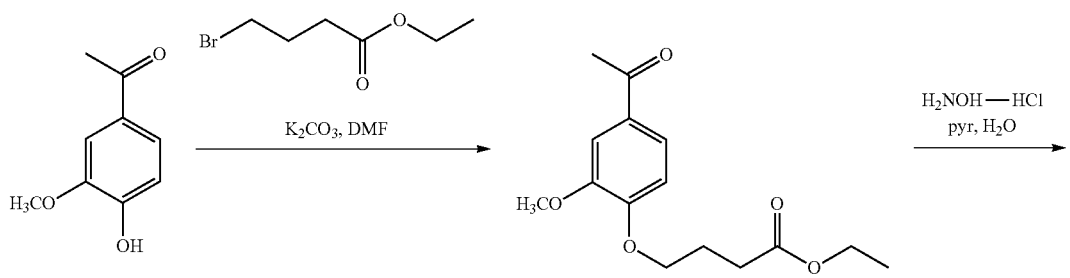

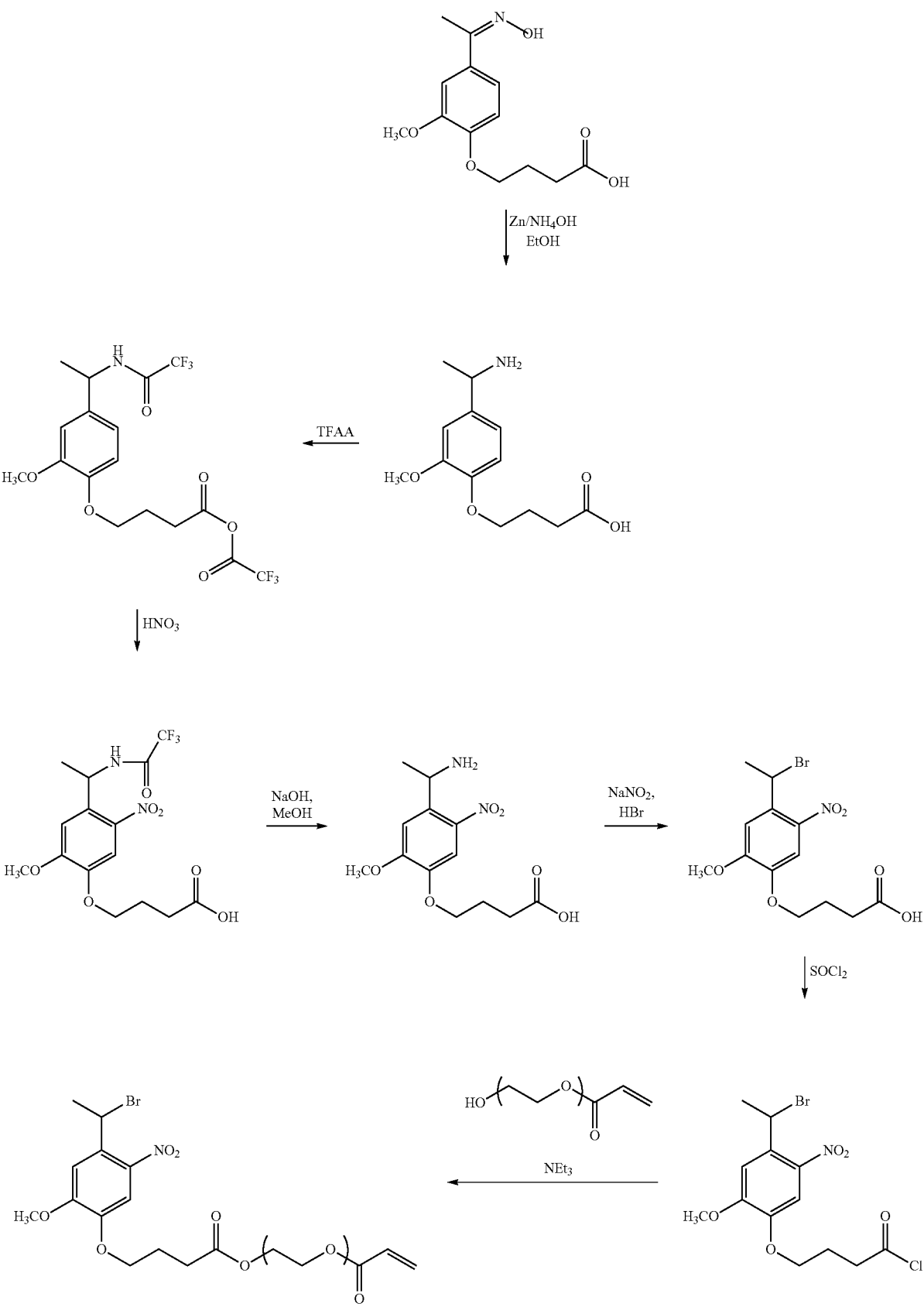

Scheme 3. Synthesis of poly(ethylene glycol) monoacrylate-6-chloro-7-hydroxycoumarin-3-carboxylate

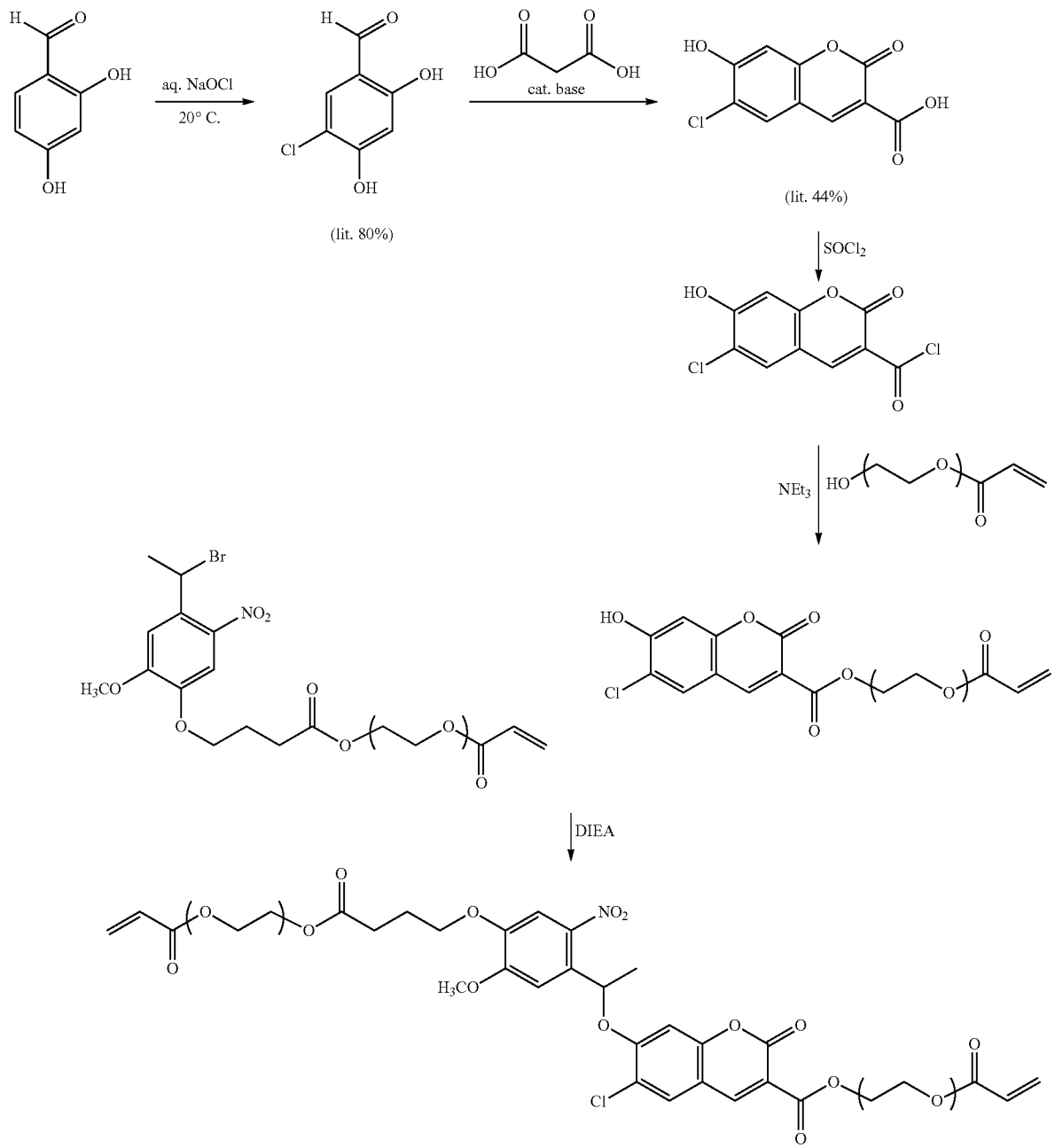

Synthesis of a fluorophore that is subsequently coupled to a photodegradable group for degradation via single and 2-photon photolysis is shown in Scheme 3. The fluorophore, poly(ethylene glycol)monoacrylate 6-chloro-7-hydroxycoumarin-3-carboxylate, was synthesized by chlorination of 2,4-dihydroxy benzaldehyde using sodium hypochlorite under acidic conditions. The resulting 5-chloro-2,4-dihydroxybenzaldehyde was condensed with malonic acid catalyzed by aniline to obtain 6-chloro-7-hydroxycoumarin-3-carboxylate, which was converted to the acid chloride using thionyl chloride, and used to esterify poly(ethylene glycol) monoacrylate (Scheme 3).

Synthesis of the photodegradable group, poly(ethylene glycol)monoacrylate-4-(2-methoxy-5-nitro-4-(2-chloroethyl)phenoxy butanoate, is shown in Scheme 4.

Synthesis of ethyl 4-(4-ethanoyl-2-methoxyphenoxy). Acetovanillone (16.6 g, 0.10 mol), potassium carbonate (30.0 g, 0.22 mol) and ethyl-4-bromobutyrate (17 mL, 0.12 mol) were combined in dimethylformamide (50 mL) and stirred under Argon for 17.5 h. The reaction was poured into water (800 mL) and stirred for 24 h. The product was isolated by filtration to yield ethyl 4-(4-ethanoyl-2-methoxyphenoxy) butanoate (27.5 g, 98%) as a white powder. $^1$H NMR (δ, ppm): 1.28 (t, $CO_2CH_2CH_3$), 2.21 (p, $ArOCH_2CH_2CH_2$), 2.56 (t, ArOCH$_2$CH$_2$CH$_2$), 2.60 (s, ArCOCH$_3$), 3.92 (s, ArOCH$_3$), 4.13 (t, ArOCH$_2$), 4.18 (q, CO$_2$CH$_2$), 6.92 (d, aromatic H ortho to ArOCH$_2$), 7.54 (s, aromatic H ortho to ArOCH$_3$), 7.58 (d, aromatic H ortho to ArCOCH$_3$).

Synthesis of ethyl 4-(4-ethanoyl-2-methoxy-5-nitrophenoxy)butanoate. 70% Nitric acid (60 mL) was cooled in an ice bath. Ethyl 4-(4-ethanoyl-2-methoxylphenoxy)butanoate (21 g, 0.075 mol) was added in portions over 20 minutes. The solution was stirred for 1.5 h while monitoring the temperature, which did not rise above 22° C. The solution was cautiously poured into water (800 mL), which was then cooled to 4° C. for several hours. The product was collected via filtration and recrystallized from ethanol (250 mL) to yield ethyl 4-(4-ethanoyl-2-methoxy-5-nitrophenoxy)butanoate (11.04 g, 45.3%) as a yellow flocculent powder. $^1$H NMR ($\delta$, ppm): 1.31 (t, CO$_2$CH$_2$CH$_3$), 2.21 (p, ArOCH$_2$CH$_2$CH$_2$), 2.52 (s, ArCOCH$_3$), 2.56 (t, ArOCH$_2$CH$_2$CH$_2$), 3.98 (s, ArOCH$_3$), 4.19 (m, ArOCH$_2$ and CO$_2$CH$_2$), 6.76 (d, aromatic H ortho to ArOCH$_2$), 7.65 (s, aromatic H ortho to ArOCH$_3$).

Synthesis of ethyl 4-(4-(1-hydroxyethyl)-2-methoxy-5-nitrophenoxy)butanoic acid. Sodium borohydride (0.8 g 0.084 mol hydride) was added in portions to ethyl 4-(4-ethanoyl-2-methoxy-5-nitrophenoxy)butanoate (10.8 g, 0.033 mol) dissolved in ethanol (200 mL) under argon. After 24 h, TLC (10:1 CH$_2$Cl$_2$:acetone eluent) indicated incomplete conversion. The reaction was warmed gently and additional sodium borohydride (0.2 g 0.021 mol hydride) was added. After 24 hours, the reaction was poured into water (800 mL) and a yellow precipitate formed. The precipitate was isolated via filtration to yield 4-(4-(1-hydroxyethyl)-2-methoxy-5-nitrophenoxy)butanoate as a yellow powder, and used without further purification. $^1$H NMR ($\delta$, ppm): 1.29 (t, CO$_2$CH$_2$CH$_3$), 1.59 (d, CHCH$_3$), 2.23 (p, ArOCH$_2$CH$_2$CH$_2$), 2.58 (t, ArOCH$_2$CH$_2$CH$_2$), 4.00 (s, ArOCH$_3$), 4.14 (m, ArOCH$_2$), 4.20 (q, CO$_2$CH$_2$), 5.59 (q, CHCH$_3$), 7.32 (d, aromatic H ortho to ArOCH$_2$), 7.60 (s, aromatic H ortho to ArOCH$_3$). The 4-(4-(1-hydroxyethyl)-2-methoxy-5-nitrophenoxy)butanoate was dissolved in a mixture of trifluoroacetic acid (10 mL) and water (100 mL) and heated to 80° C. for 18 h, at which point $^1$H NMR indicated incomplete conversion. Additional TFA (5 mL) was added, and the reaction was continued for 24 h. After 24 h, the reaction was cooled to room temperature to form a precipitate which was collected via filtration. The precipitate was lyophilized to yield 4-(4-(1-hydroxyethyl)-2-methoxy-5-nitrophenoxy)butanoic acid (8.53 g (86%) as a yellow powder. $^1$H NMR ($\delta$, ppm, acetone d-6): 1.53 (d, CHCH$_3$), 2.12 (p, ArOCH$_2$CH$_2$CH$_2$), 2.55 (t, ArOCH$_2$CH$_2$CH$_2$), 4.03 (s, ArOCH$_3$), 4.16 (m, ArOCH$_2$), 5.47 (q, CHCH$_3$), 7.47 (d, aromatic H ortho to ArOCH$_2$), 7.59 (s, aromatic H ortho to ArOCH$_3$).

Synthesis of 4-(4-(1-chloroethyl)-2-methoxy-5-nitrophenoxy)butanoyl chloride. 4-(4-(1-Hydroxyethyl)-2-methoxy-5-nitrophenoxy)butanoic acid (1.72 g, 5.76 mmol) was added all at once to a solution of methylene chloride (15 mL), dimethylformamide (1 drop) and thionyl chloride (2.2 mL, 0.030 mol) to form a heterogenous solution. After three hours, the solution became homogenous. The methylene chloride was removed via rotary evaporation, and the resulting 4-(4-(1-chloroethyl)-2-methoxy-5-nitrophenoxy)butanoyl chloride was used without further purification. $^1$H NMR ($\delta$, ppm,): 1.88 (d, CHCH$_3$), 2.21 (p, ArOCH$_2$CH$_2$CH$_2$), 2.56 (t, ArOCH$_2$CH$_2$CH$_2$), 4.00 (s, ArOCH$_3$), 4.13 (m, ArOCH$_2$), 5.92 (q, CHCH$_3$), 7.29 (d, aromatic H ortho to ArOCH$_2$), 7.51 (s, aromatic H ortho to ArOCH$_3$).

Synthesis of bis-4-(4-(1-chloroethyl)-2-methoxy-5-nitrophenoxy)butanoyl-poly(ethylene glycol). 4-(4-(1-chloroethyl)-2-methoxy-5-nitrophenoxy)butanoyl chloride (1.94 g, 5.8 mmol) in methylene chloride (10 mL) was added dropwise to a solution of poly(ethylene glycol) 2000 (4.8 g, 2.4 mmol) and triethylamine (1 mL, 7.1 mmol) while cooling to 0° C. After 12 hours, the product was precipitated into cold (0° C.) diethyl ether (500 mL) and collected via filtration to yield bis-4-(4-(1-chloroethyl)-2-methoxy-5-nitrophenoxy)butanoyl-poly(ethylene glycol) (6.05 g, 81%).

Scheme 4. Synthesis of poly(ethylene glycol) monoacrylate-4-(2-methoxy-5-nitro-4-(2-chloroethyl)phenoxy butanoate).

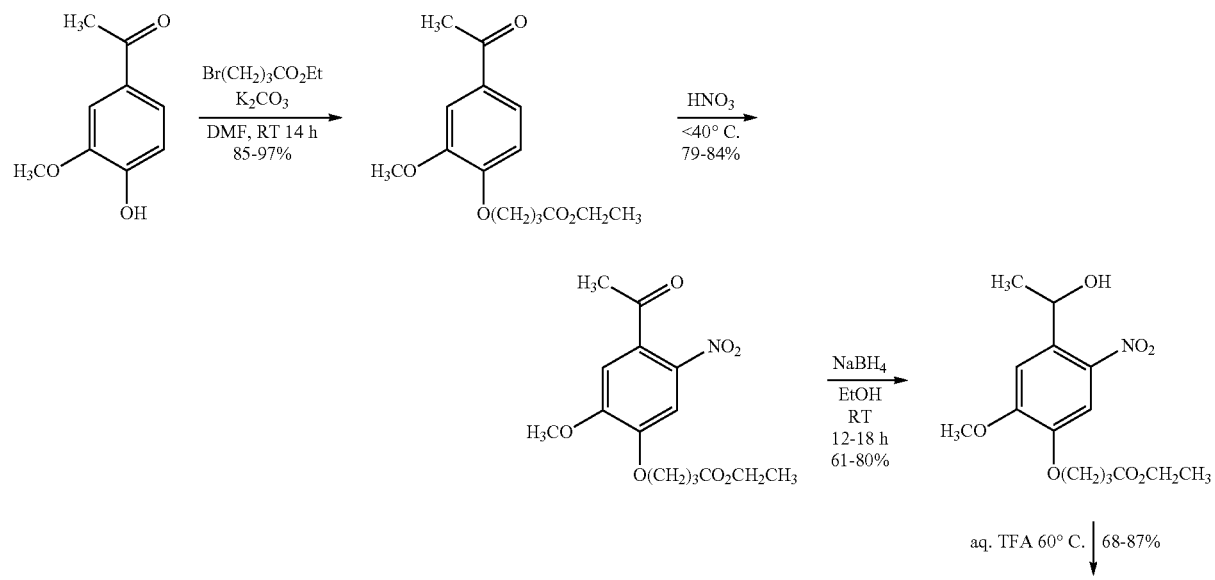

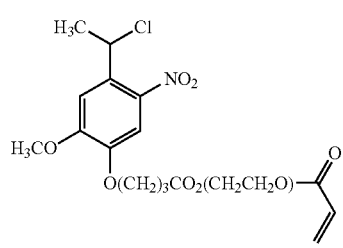 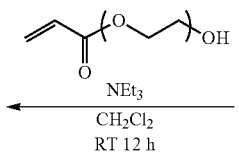 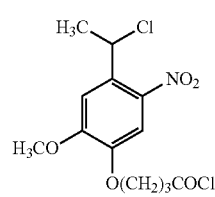 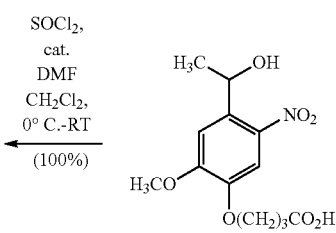

The synthesis of fluorescein poly(ethylene glycol) monoacrylate, is shown in Scheme 5.

Synthesis of Poly(ethylene glycol) acrylate succinate. Poly(ethylene glycol) 375 acrylate (5.6 g, 15 mmol) and DMAP (0.25 g, 2.0 mmol) were dissolved in chloroform (100 mL). Succinic anhydride (1.8 g, 18 mmol) was added in portions. The reaction was heated to reflux for 14 h. After cooling the reaction mixture was washed with dil. aq. HCl (2×50 mL) and dried over sodium sulfate. The solvent was removed via rotary evaporation to yield poly(ethylene glycol) acrylate succinate (6.6 g, 92%) as a viscous oil.

Synthesis of Poly(ethylene glycol) acrylate succinyl fluorescein. Poly(ethylene glycol) acrylate succinate (5.2 g, 11 mmol), fluorescein (9.1 g, 27 mmol), dimethylaminopyridine (0.077 g, 0.6 mmol) and dicyclohexylcarbodiimide (2.7 g, 13 mmol) were dissolved in 95 mL THF and stirred at room temperature under argon for 22 h. The THF was removed via rotary evaporation and the mixture precipitated into methylene chloride. Excess fluorescein was removed via filtration, and the solvent removed via rotary evaporation. The crude product was taken into chloroform, filtered and concentrated five times to remove excess fluorescein, and the same procedure was repeated using acetone, as fluorescein has low solubility in both chloroform and acetone. The solvent was removed via rotary evaporation to yield poly(ethylene glycol) acrylate succinyl fluorescein.

Scheme 5. Synthesis of poly(ethylene glycol) monoacrylate fluorescein.

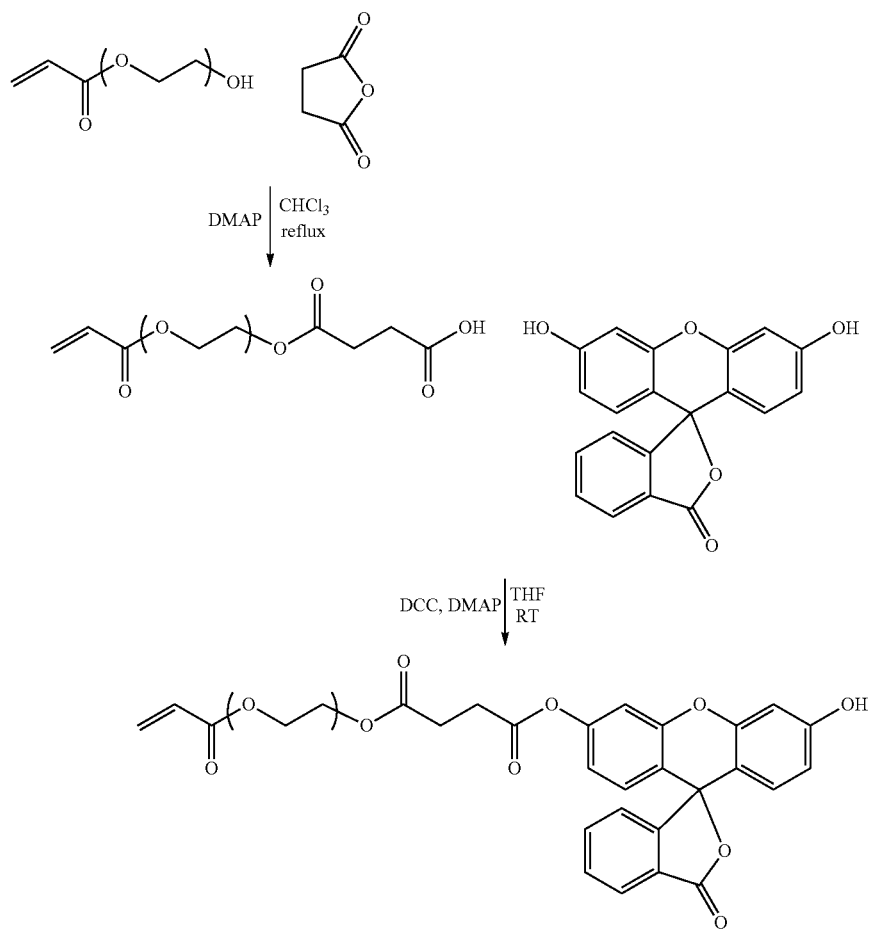

The synthesis of 6-chloro-7-hydroxy-3-coumarin carboxylic acid is shown in Scheme 6.

Synthesis of 5-chloro-2,4-dihydroxybenzaldehyde. Sodium hypochlorite (75 mL, 0.055 mol) and piperidine (4.68 g, 0.055 mol) were cooled to 0° C., combined cautiously and added dropwise over 2 h to a solution of 2,4,-dihydroxybenzaldehyde (6.91 g, 0.05 mol) in 50% aqueous sulfuric acid (150 mL) while cooling to 0° C. After three additional hours, the precipitate was collected via filtration in quantitative yield. $^1$H NMR indicates that it is about 65% 5-chloro-2,4-dihdroxybenzaldehyde, with the balance being 3-chloro-2,4-dihdroxybenzaldehyde. The product can be purified via column chromatography and/or repeated recrystallizations from toluene. However, the 3-chloro-2,4-dihdroxybenzaldehyde does not react in the next reaction, so the product was used without further purification.

Synthesis of 6-chloro-7-hydroxycoumarin-3-carboxylate. Chloro-2,4-dihdroxybenzaldehyde (mixture of 3- and 5-isomers, 6.59 g, 0.038 mol), malonic acid (8.02 g, 0.077 mol) and aniline (1 mL) were combined in pyridine (30 mL) and stirred at RT. After 3 d, the reaction was acidified using HCl and the product was collected via filtration to yield 6-chloro-7-hydroxycoumarin-3-carboxylate (5.14 g, 55.9% overall, 86% based on starting ratio of 5-chloro-2,4-dihydroxybenzaldehyde) as a yellow powder.

Synthesis of poly(ethylene glycol)bis-6-chloro-7-hydroxycoumarin-3-carboxylate. 6-Chloro-7-hydroxycoumarin-3-carboxylate (2 equivalents) dicyclohexylcarbodiimide (2.5 equivalents), dimethylaminopyridine (0.1 equivalent), and poly(ethylene glycol) (molecular weight=2000 g/mol, 1 equivalent) were combined in methylene chloride. The reaction was allowed to stir for 18 h under argon, and then precipitated into cold diethyl ether. The precipitate was collected via filtration, dissolved in water, and purified via dialysis. The dissolved product was then lyophilized to yield poly(ethylene glycol)bis-6-chloro-7-hydroxycoumarin-3-carboxylate as a bright yellow solid.

Scheme 6. Synthesis of 6-chloro-7-hydroxy-3-coumarin carboxylic acid, and the coupling of 6-chloro-7-hydroxy-3-coumarin carboxylic acid with poly(ethylene glycol) and poly(ethylene glycol) monoacrylate.

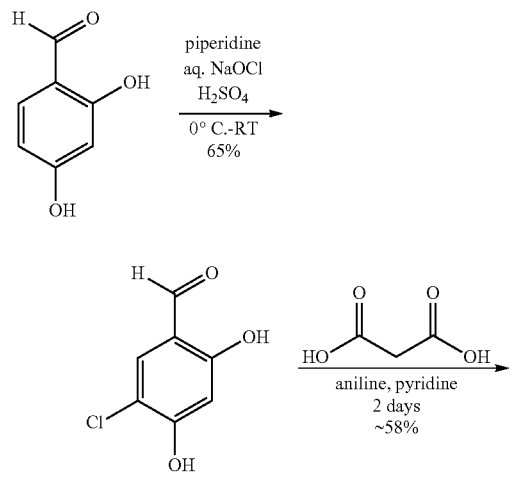

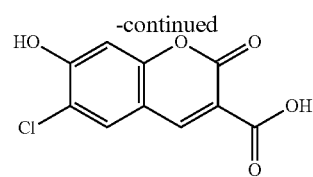

-continued

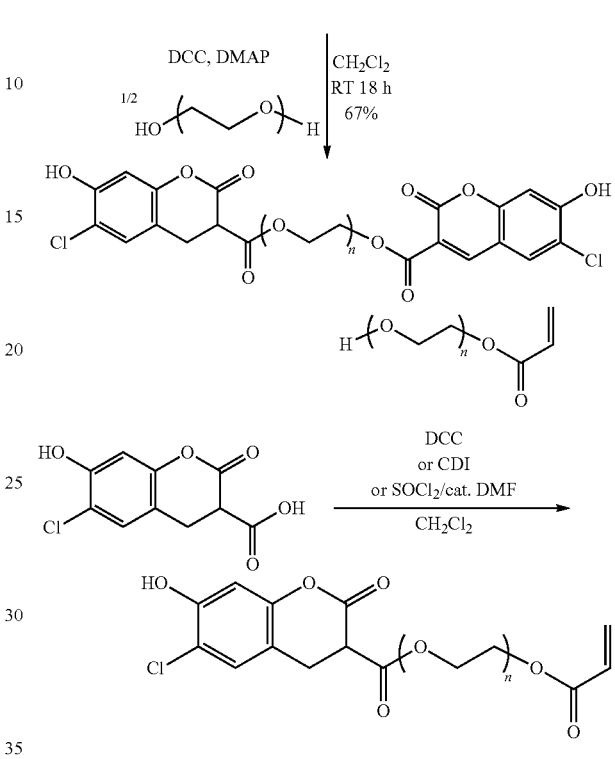

The photodegradable group can be coupled with compounds such as therapeutic agents, fluorophores, or chromagenic agents, for release upon photodegradation. Some examples are shown in Scheme 7-12.

General procedure for coupling compounds to poly(ethylene glycol) with attached photodegradable group(s): The compound of interest, which has a free hydroxyl group is dissolved in THF and deprotonated with sodium hydride. The PEG with attached photodegradable group is added dropwise to the solution, which is then allowed to stir at room temperature and/or heated gently. After six to 24 hours, the product is precipitated into cold diethyl ether. The product may be used without further purification, or purified using dialysis.

The tethered compounds can incorporated into hydrogels or other networks or scaffolds, or linear or branched polymeric systems for controlled release. The general procedure is the same; the alcohol group of a substrate is deprotonated using sodium hydride with tetrahydrofuran as a solvent; this alkoxide ion undergoes nucleophilic substitution at the 2-chloroethyl position of the poly(ethylene glycol) monoacrylate-4-(2-methoxy-5-nitro-4-(2-chloroethyl)phenoxy butanoate to produce the photodegradable macromers. Scheme 7 shows the synthesis of tethered dexamethasone. Scheme 8 shows synthesis of photodegradable poly(ethylene glycol)diacrylate. Scheme 9 shows the synthesis of a photocaged poly(ethylene glycol)bis-coumarin. Scheme 10 shows synthesis of photocaged coumarin incorporated into a poly(ethylene glycol)diacrylate. Scheme 11 shows synthesis of photocaged fluorescein incorporated into a poly(ethylene glycol)diacrylate. Scheme 12 shows synthesis of photodegradable poly(ethylene glycol)diacrylate that releases poly(ethylene glycol) upon degradation.

Scheme 7. Synthesis of tethered dexamethasone.
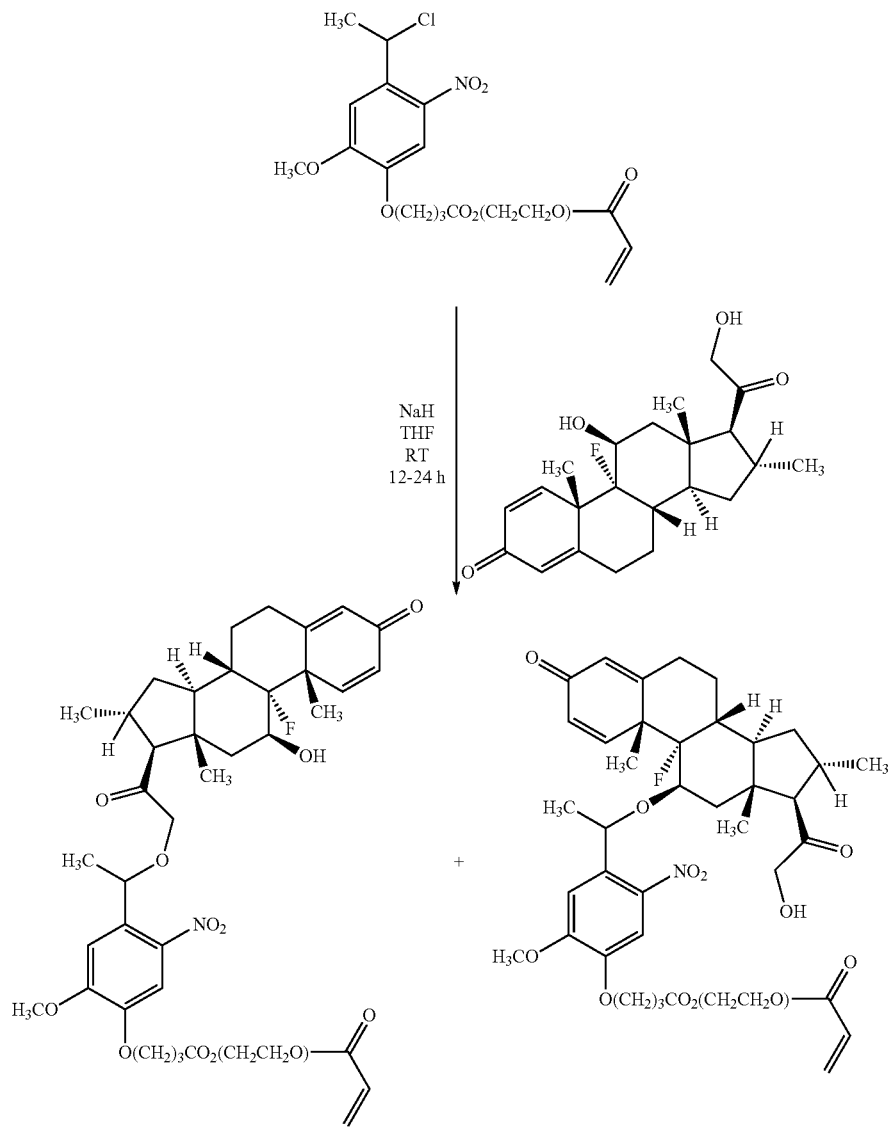
Scheme 8. Synthesis of photodegradable poly(ethylene glycol)diacrylate.
-continued
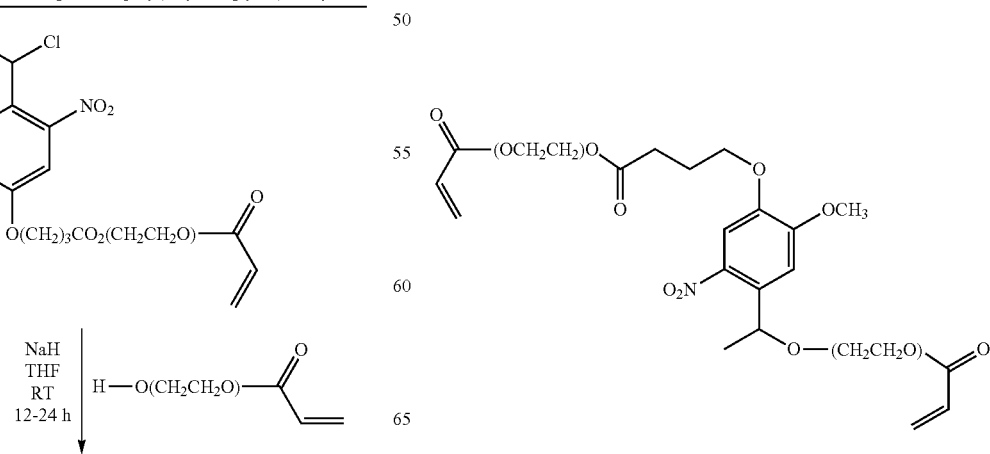

Scheme 9. Synthesis of photocaged poly(ethylene glycol) bis-coumarin.
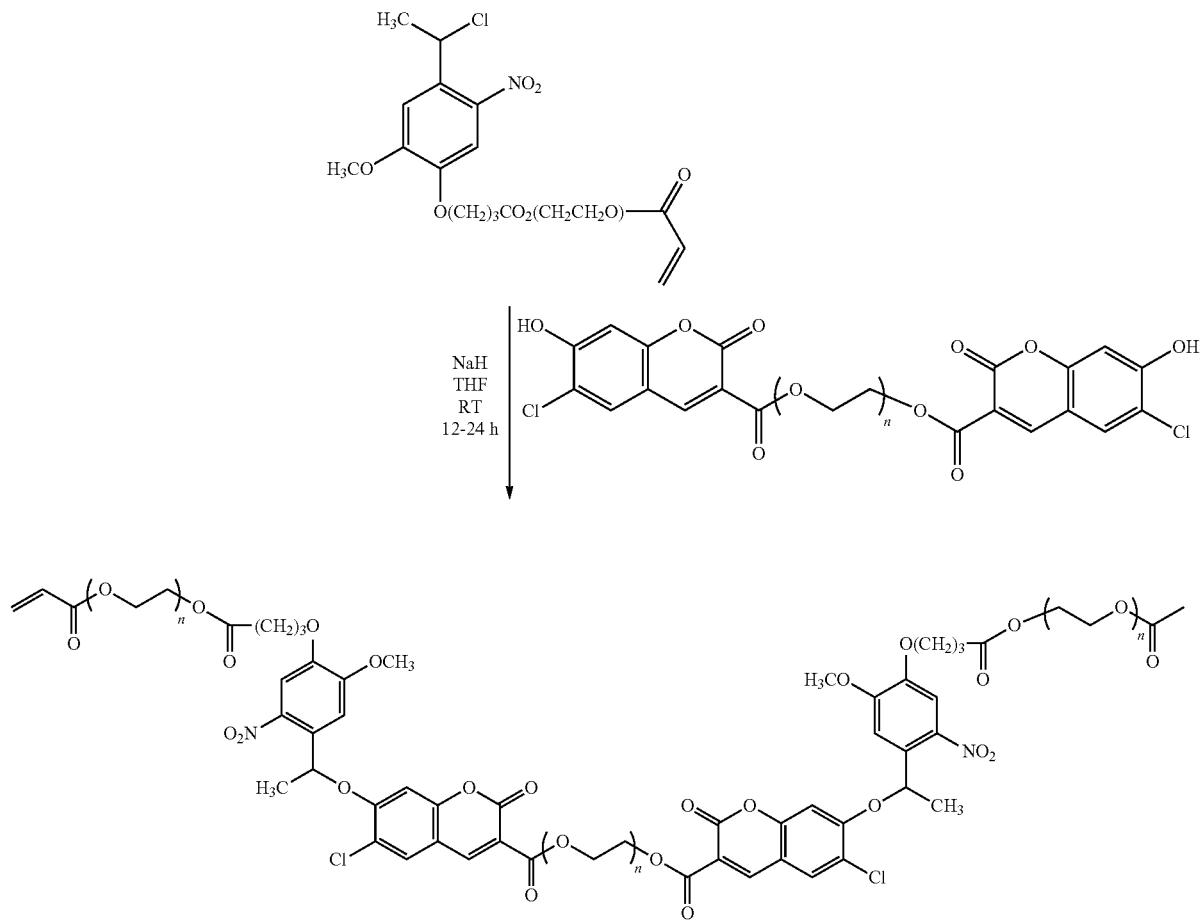
Scheme 10. Synthesis of photocaged coumarin incorporated into a poly(ethylene glycol) diacrylate.
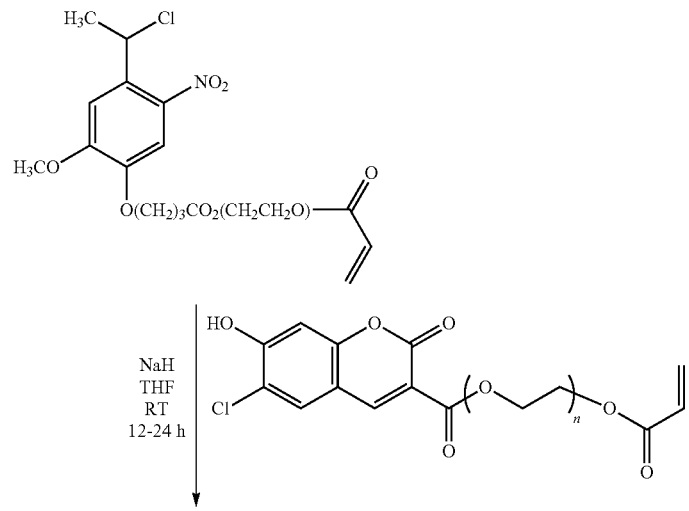

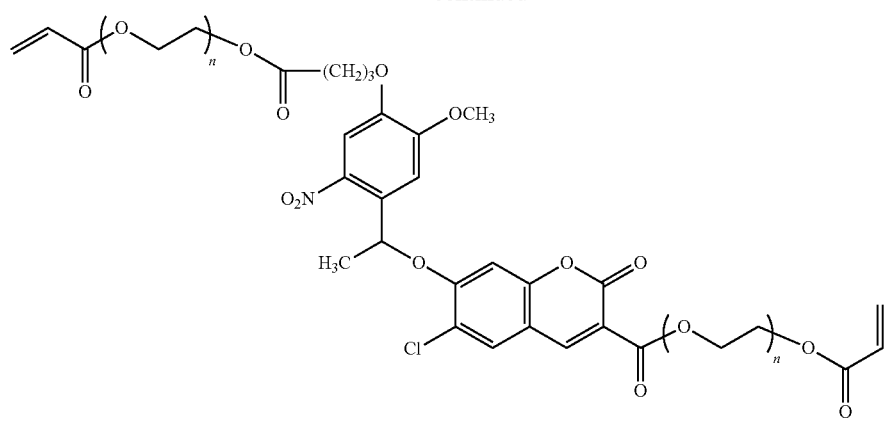
Scheme 11. Synthesis of a photocaged fluorescein incorporated into a poly(ethylene glycol) diacrylate.
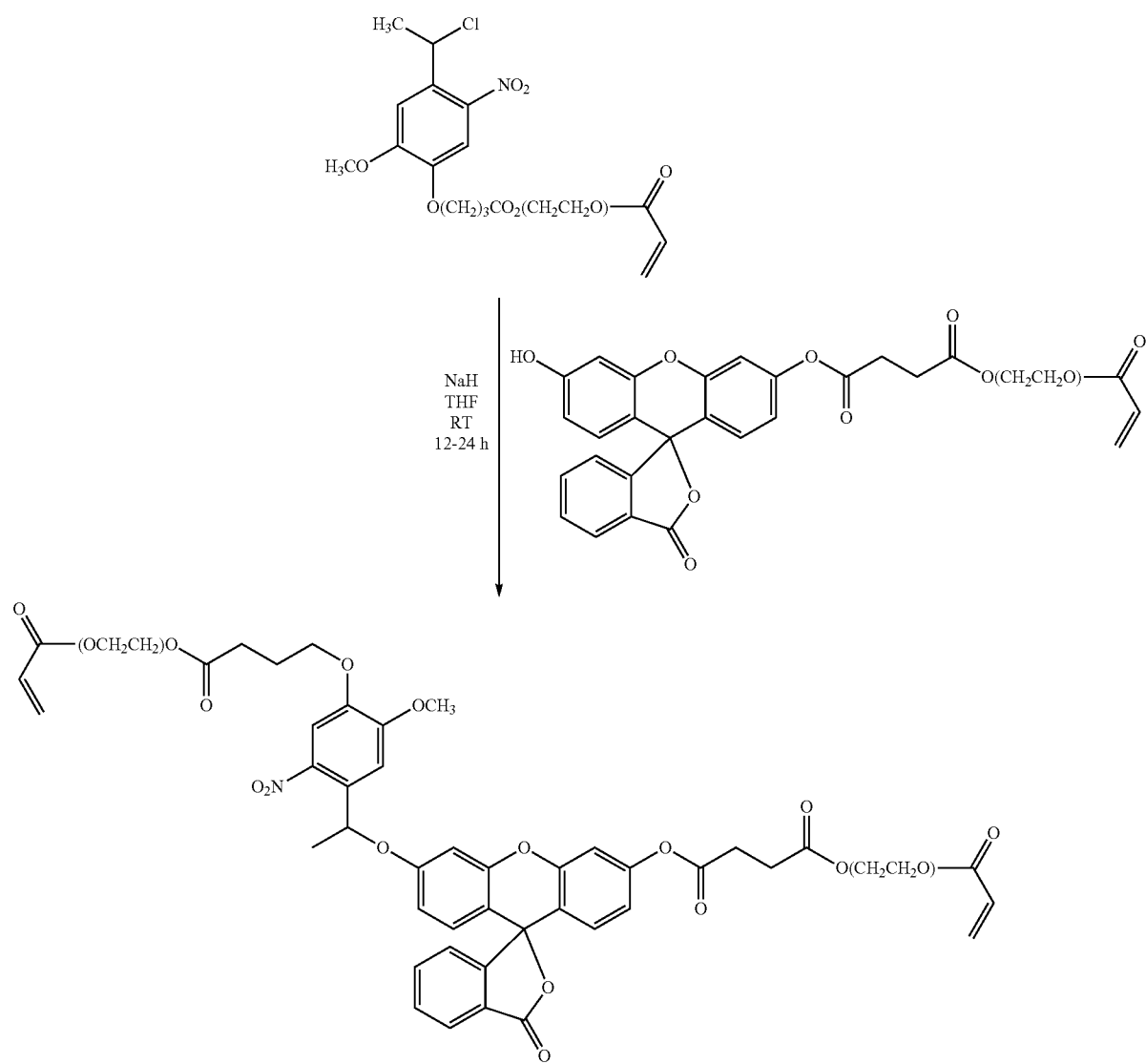

Scheme 12. Synthesis of photodegradable poly(ethylene glycol) diacrylate that releases poly(ethylene glycol) upon degradation.

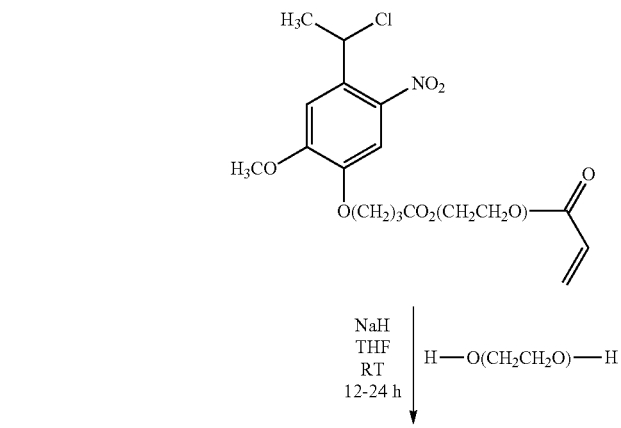

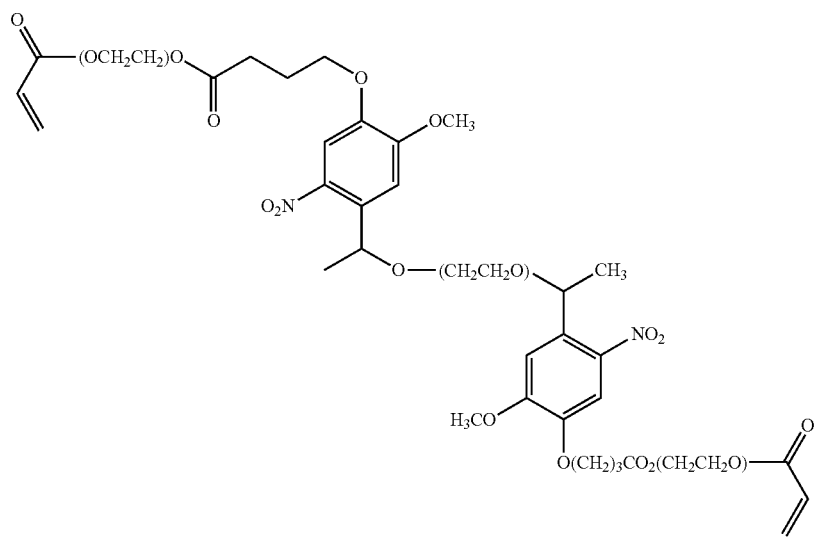

Many moieties in these chemical structures can be varied, as known in the art. For example, the poly(ethylene glycol) backbone chains can be substituted with any polymer or copolymer, as long as there is a functional group capable of reacting with the photodegradable group directly or through a suitable linker. The therapeutic agents, caged groups, reactive end groups, backbone structure and photodegradable groups can all be varied, as known in the art. The degradation rate of the photodegradable group can be tailored by changing the structure, as shown in Scheme 13, where R and R' are suitable substituents such as a caged or therapeutic group or a reactive end group or backbone, or combination thereof, with or without a linker.

Scheme 13. Photodegradation rate changes with structure. Both axes show decreasing uncaging rate towards the arrows.

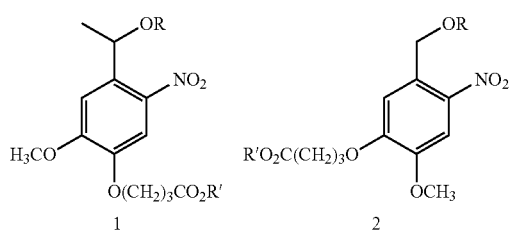

-continued

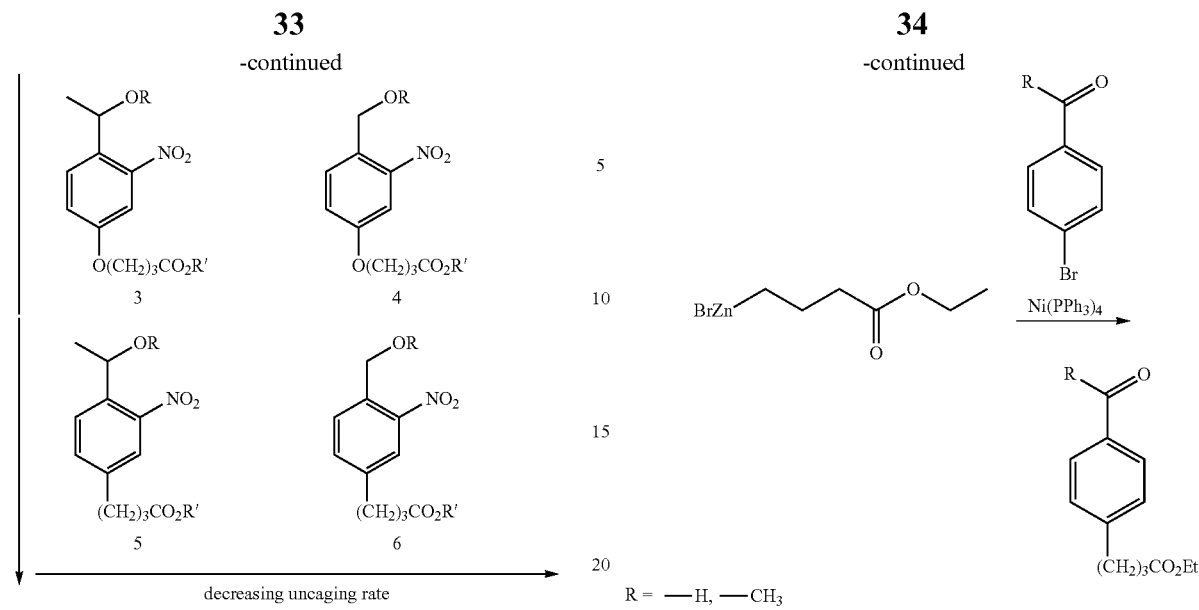

decreasing uncaging rate

In the structures shown above, photodegradation occurs at the benzyl ether position; changing this from a secondary to a primary ether will change the reactivity (first column in Scheme 13 is a secondary ether, second column in Scheme 13 is a primary); decreasing the number of aryl-ether groups in the photodegradable groups also decreases the rate of photodegradation. All compounds shown in the Schemes and Figures herein can be synthesized using methods known in the art and described herein. For example, to synthesize compound 2, the same synthetic route as for compound 1 is used, but instead of acetovanillone as the starting material, 3-hydroxy-4-methoxybenzaldehyde is used. To synthesize compound 3, the same synthetic route is used, but instead of acetovanillone as the starting material, 4-hydroxyacetophenone is used. To synthesize compound 4, the same synthetic route is used, but instead of acetovanillone as the starting material, 4-hydroxybenzaldehyde is used. To synthesize compound 5,4-bromoacetophenone can be alkylated with ethyl-4-bromobutyrate using a Negishi coupling (see below); the rest of the synthetic route is then used to obtain the product. To synthesize compound 6,4-bromobenzaldehyde is alkylated with ethyl-4-bromobutyrate using a Negishi coupling; the rest of the synthetic route is then used to obtain the product.

Since the rates of uncaging may differ by orders of magnitude, the rate of release of a drug, for example can be tuned to the desired purpose. For example, one caged structure that uncages rapidly can be used for releasing a drug (compound having fast uncaging properties, for example compound 1 in Scheme 13), simultaneously with one for release of another drug and/or network degradation (compound having slow uncaging properties, for example, compound 6 in Scheme 13).

Simple Negishi coupling will produce the least reactive photocages:

Scheme 14

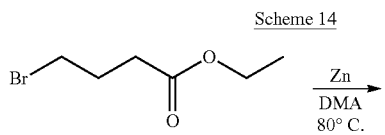

All of the reagents used in the routes above are commercially available, but other structures, where the aryl ether (or alkyl chain) is located on a different position of the ring, can also be synthesized using methods known in the art and described herein.

Examples of Degradation

Although applicant does not wish to be bound by theory, a proposed mechanism of degradation of nitrophenylethyl based photocages is shown in Scheme 15 and is described in Zhao, et al., J. Am. Chem. Soc. (2004) 126: 4653-4663. Upon UV excitation, the substituted nitrophenylethyl groups forms an aci-nitro intermediate which decays to generate X- and 2-nitrosoacetophenone.

Scheme 15. Degradation mechanism of nitrophenylethyl photocage.

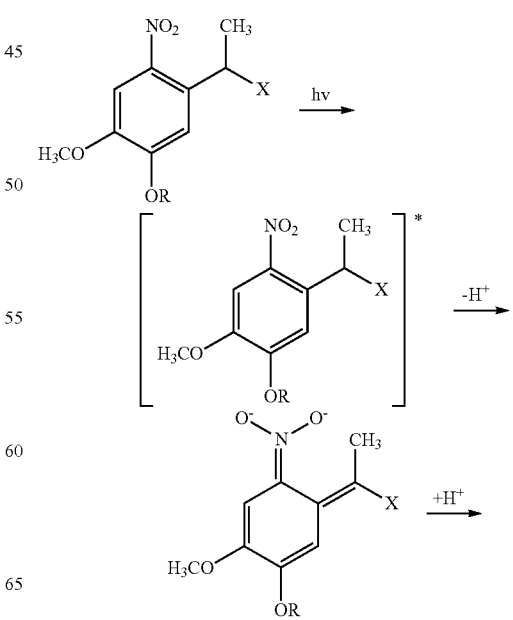

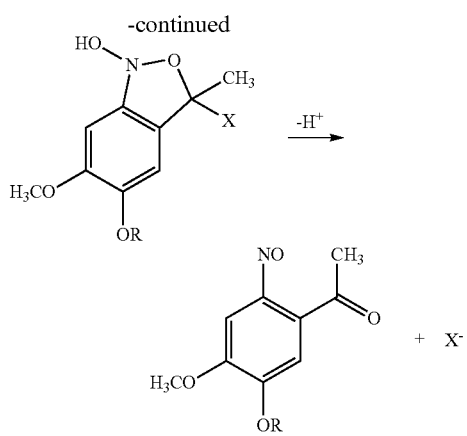

Figure 4:
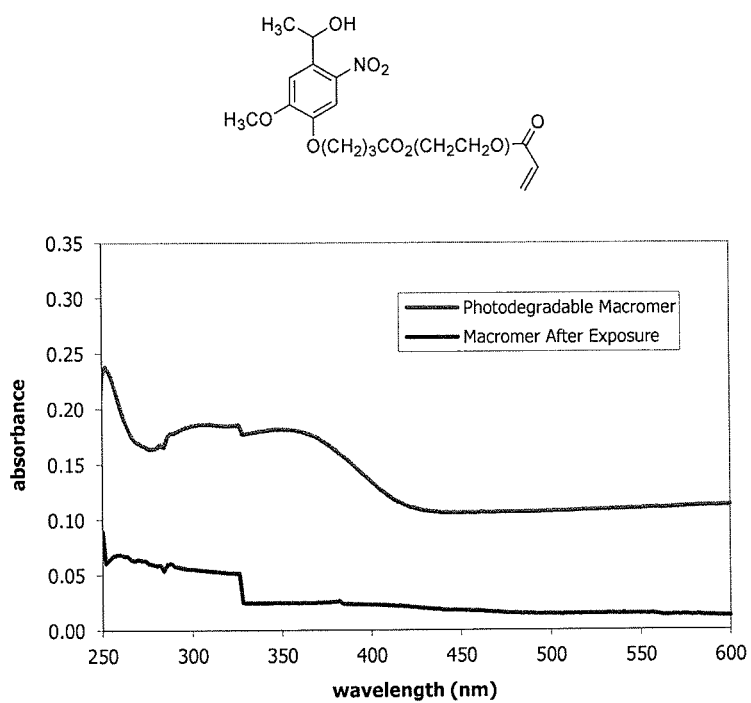
FIG. 4 shows the UV-Visible Absorption of poly(ethylene glycol) monoacrylate-4-(2-methoxy-5-nitro-4-(2-hydroxyethyl)phenoxy butanoate before and after exposure to 365 nm light (5 minutes).

The UV-Vis absorption spectra for poly(ethylene glycol) monoacrylate-4-(2-methoxy-5-nitro-4-(2-hydroxyethyl) phenoxy butanoate are shown in FIG. 4. The top line is the spectrum of poly(ethylene glycol)monoacrylate-4-(2-methoxy-5-nitro-4-(2-hydroxyethyl)phenoxy butanoate in water; the bottom line is the spectrum after the solution has been exposed to 365 nm light for 5 minutes. The poly(ethylene glycol)monoacrylate-4-(2-methoxy-5-nitro-4-(2-hydroxyethyl)phenoxy butanoate is clearly degrading; hydroxide anion is released.

General Procedure for Controlled 2-D Degradation using a photomask: A photomask is contacted with the surface of the hydrogel. The gel can be degraded using a 5 cm collimated flood exposure source coupled to an optical mask alignment system (Optical Associates, Inc. San Jose, Calif.), which generates 50-70 mW cm-2 of radiation (365 nm). An adjustable reaction chamber facilitates well-defined control over degradation. The spacing between the photomask and chamber bottom is controlled by micromanipulators coupled to a height sensor and the entire reaction chamber is integrated with the theta and lateral controls of the Mask aligner. Photomasks are made using emulsion films (Polychrome V; Kodak, Rochester, N.Y.) exposed with a high-resolution He—Ne red laser diode commercial plotter.

3-D Lithography may be accomplished using a series of photomasks with the mask alignment system described above, or through the use of a two-photon laser scanning microscope.

Figure 5:
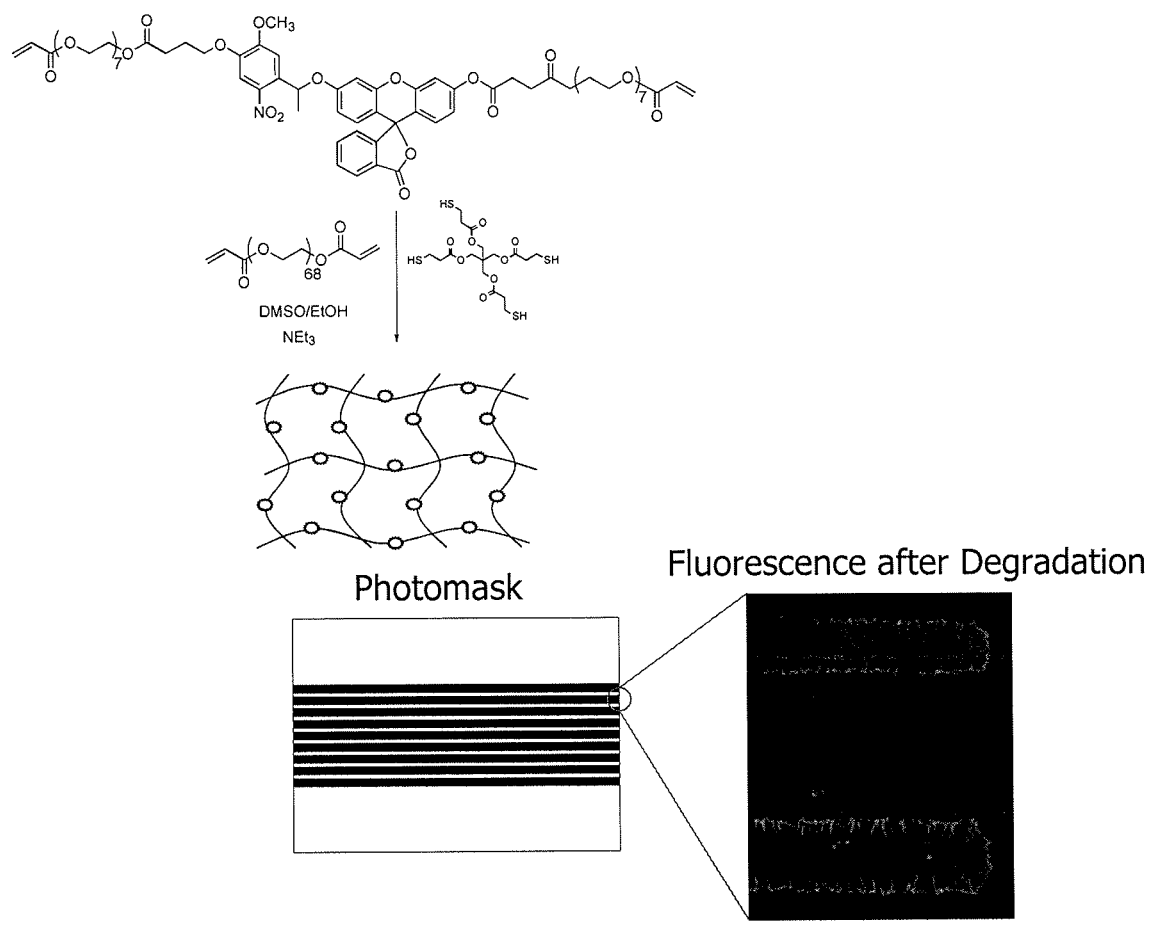
FIG. 5 shows one example of spatial control over photodegradation: exposed areas show increased fluorescence.

Spatial Control Over Degradation. Poly(ethylene glycol) diacrylate with the photodegradable 2-methoxy-5-nitro-4-(2-fluoresceinoxyethyl)phenoxy butanoate group incorporated into the middle of the macromer chain was copolymerized with poly(ethylene glycol)diacrylate using pentaerythritol tetrakis(3-mercaptopropionate) as a crosslinking agent in a pseudo-Michael addition. The polymerization solution was spin-coated onto a polycarbonate substrate. The film was exposed to 365 nm light under a photomask. If photodegradation occurs, an increase in fluorescence in the exposed areas is expected. This is shown in FIG. 5, where the areas of the film exposed to the photomask show an increase in fluorescence.

Temporal Control Over Degradation. The photocaged bis-coumarin poly(ethylene glycol)diacrylate shown in Scheme 16 was copolymerized with poly(ethylene glycol)diacrylate using pentaerythritol tetrakis(3-mercaptopropionate) as a crosslinking agent in a pseudo-Michael addition. The resulting hydrogel was immersed in water and exposed to 365 nm light. After 30 seconds exposure, the solution was slightly fluorescent blue. After 10 minutes exposure, the solution became more strongly fluorescent blue (data not shown), indicating the release of poly(ethylene glycol)bis-coumarin increases with increasing exposure time.

Scheme 16.

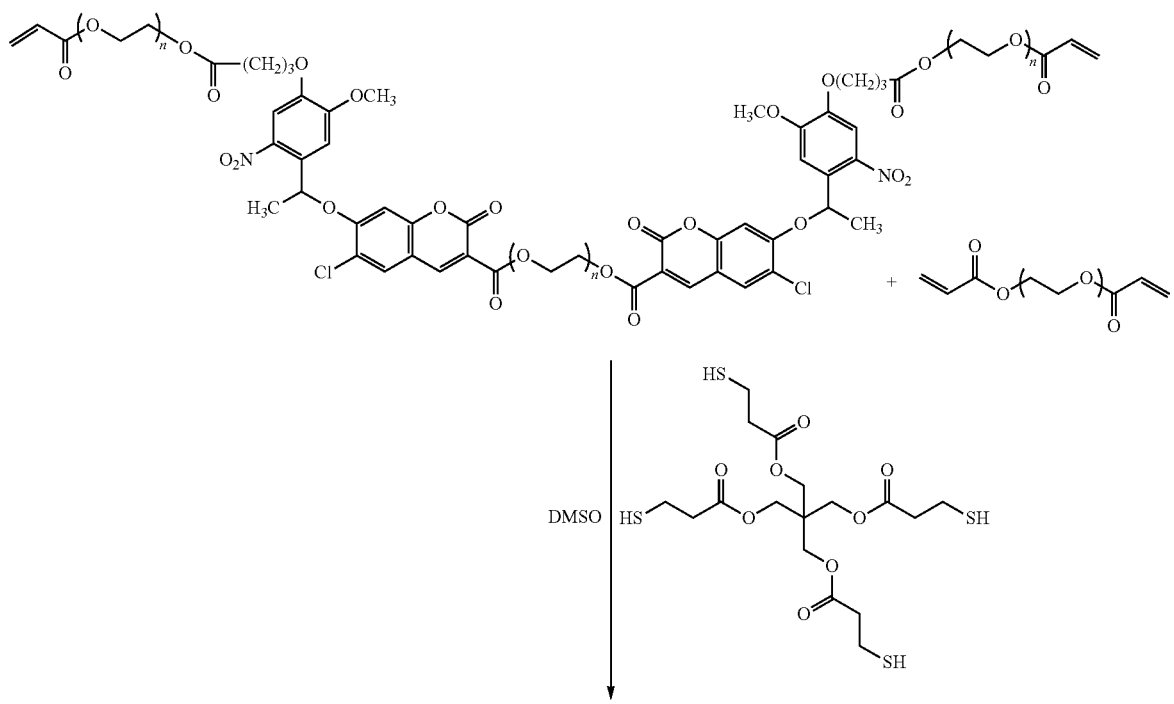

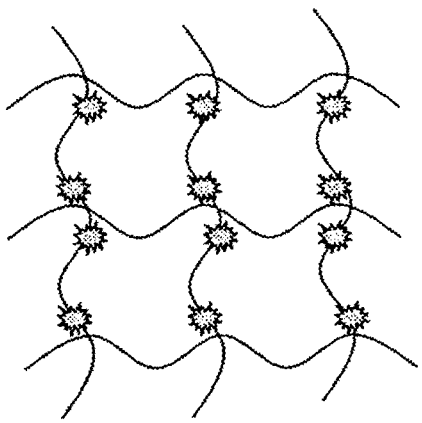

Figure 6:
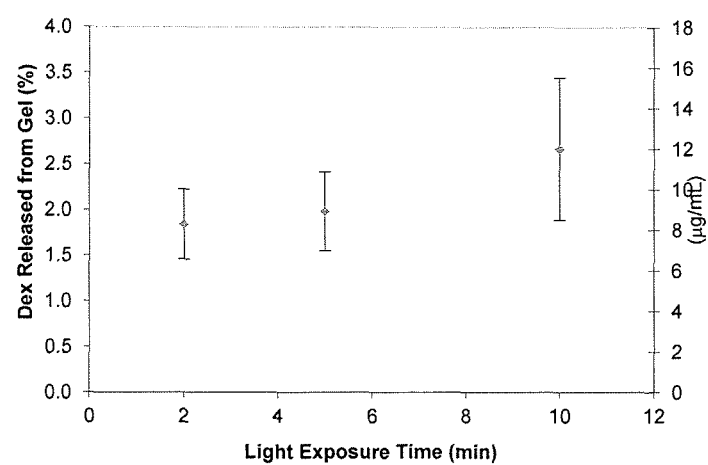
FIG. 6 shows the release of dexamethasone with increasing exposure time.

Release of a therapeutic molecule. Tethered dexamethasone was polymerized into a poly(ethylene glycol) gel network using pentaerythritol tetrakis(3-mercaptopropionate) as a crosslinking agent in a pseudo-Michael addition to form discs, approximately 5 mm by 1 mm. Unreacted monomer was leached from the hydrogel using methanol. The loading concentration of releasable dexamethasone ranged from 5-640 μg per gel; each gel was suspended in 0.5 mL solvent. Each gel was exposed to UV light for 12 minutes, and the resulting release of dexamethasone quantified by HPLC. Only the gels with highest loading released detectible amounts of dexamethasone (the remaining concentrations were below the detection limits of the HPLC detector). After 12 minutes, 21% of the dexamethasone was released. This concentration, 273 μg/mL, is significantly higher than the amount shown in the literature needed to promote stem cell differentiation (100 nM) (Nuttleman, C. R.; Tripodi, M. C.; Anseth, K. S. "Dexamethasone-functionalized gels induce osteogenic differentiation of encapsulated hMSCs" J. Biomed. Mtls. Res. 2005, 76A, 183-195). If the gels are exposed for varying amounts of time, the amount of dexamethasone released increased, but the error is large. These results are shown in FIG. 6, where Dex released from Gel (%) is plotted (left) along with μg/mL (right).

Photodegradable Hydrogels

General procedure for formation of hydrogel: Formation of a hydrogel using these macromers is accomplished by reacting the acrylate end groups in a stoichiometric ratio with the thiol groups on a multifunctional thiol in water or dimethylsulfoxide. This may or may not require a catalyst as known in the art. The reactive end-groups can also be polymerized if a wavelength of light is used that does not induce photodegradation, or if polymerization is much faster than photodegradation. The solvent content of the hydrogel will vary directly with the molecular weight of the macromer. These reactions are known in the art. These solutions can be cast using a spin-coater to form a thin film, or cast into a confined geometry to form a gel.

Example: Poly(ethylene glycol)monoacrylate-4-(2-methoxy-5-nitro-4-(2-bromoethyl)phenoxy)butanoate and poly(ethylene glycol)monoacrylate 6-chloro-7-hydroxycoumarin-3-carboxylate are coupled using diispropylethylamine to obtain the photodegradable PEG diacrylate. This diacrylate is then polymerized into a network using a visible-light photoinitiator or via a Michael-type addition using multifunctional thiols. The resulting hydrogels contain crosslinks that are photolyzable by single and two-photon photolysis using the methods described herein.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, synthetic methods, and uses other than those specifically exemplified can be employed in the practice of the invention without resort to undue experimentation. All art-known functional equivalents, of any such methods, device elements, starting materials, synthetic methods, and uses are intended to be included in this invention. Whenever a range is given in the specification, for example, a temperature range, a time range, or a composition range, all intermediate ranges and subranges, as well as all individual values included in the ranges given are intended to be included in the disclosure.

Example

Signaling proteins influence a myriad of critical cell functions, including differentiation, migration, and cell fate decisions, and many of these effects are pleiotropic depending on the dose and persistence of the signal.[1-4] Thus, spatiotemporal control over protein presentation is critical to study and understand the role that these biomacromolecules play in dynamic cellular processes. Toward this end, a prevalent method to protect, target, and locally deliver proteins and other therapeutics is to load such factors in polymeric microspheres.[5,6] Such delivery vehicles enable the release of high doses of protein at specific locales, as well as controlled release over a desired time course.[7,8]

Microsphere systems, typically formed from hydrolytically degradable polymers with pre-determined release profiles, have been used in numerous controlled release applications, including in vitro delivery of factors that influence the differentiation of embryoid bodies[9] or in vivo delivery of osteogenic factors to encourage robust bone growth.[10] Corresponding to the increase in the discovery of biological factors that direct stem cell differentiation, treat a range of diseases, and encourage proper tissue morphogenesis, there has been a focus on developing advanced materials that offer precise control over the delivery of such molecules. To date, full spatiotemporal control over the release and presentation of these factors during cell culture has been limited and few systems allow experimenters to direct release in real time. As a result of the lack of more sophisticated protein delivery vehicles, it has become increasingly difficult and time consuming to determine appropriate doses and release profiles of biomacromolecules for specific applications. Further, advanced understanding of wound healing and developmental processes underscore the importance of the proper presentation of multiple cues, including proteins and co-factors or morphogen pairs, which is exceedingly difficult with current methods. Finally, few material systems allow the experimenter to introduce spatially heterogeneous gradients at any point in time that could be used to investigate how morphogens act during development and to fashion complex tissue structures ex vivo.

To circumvent these limitations and complement existing microsphere technologies, a unique delivery vehicle based on photolabile networks is presented that offers the experimenter control of entrapped biomolecule delivery in real time and in a manner that is compatible with 2D and 3D cell culture. Specifically, photodegradable, poly(ethylene glycol) (PEG) based hydrogel microspheres are fabricated that entrap and, subsequently, deliver proteins of interest on demand by exposure to selected wavelengths of light. Such delivery systems should prove beneficial for testing hypotheses related to how temporal and spatial protein presentation affects local cell function and have applied benefits for the controlled expansion and differentiation of stem cells.

Figure 9:
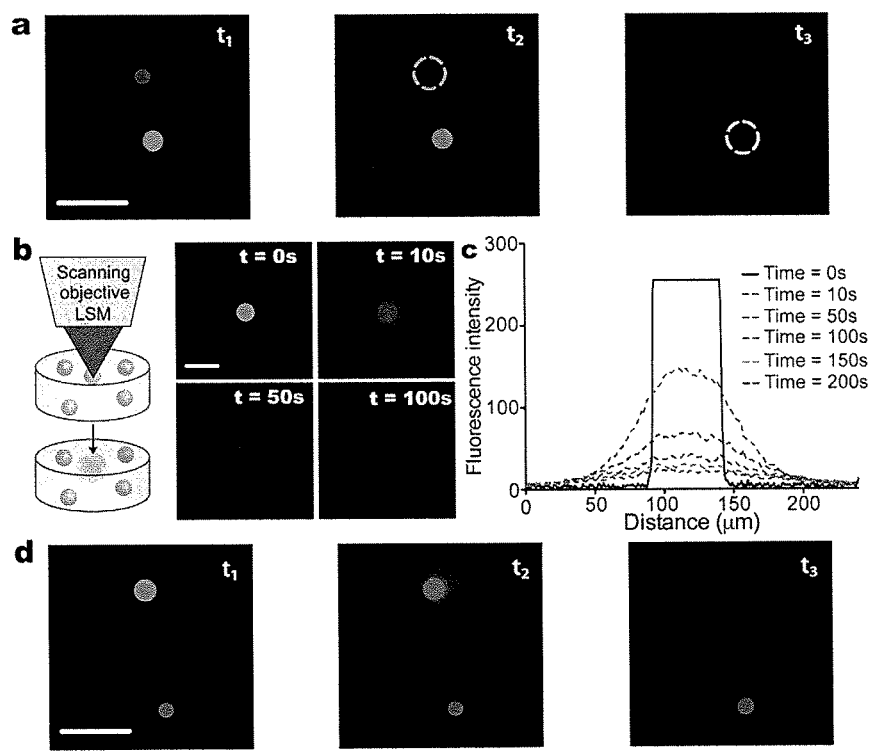
FIG. 9 shows spatially controlled degradation of photodegradable particles. (a) BSA-488 loaded microparticles were combined with BSA-594 loaded particles in a single system and focused irradiation from an LSM ($\lambda$=740 nm; two-photon) was used to erode individual particles selectively. Here, a BSA-594 loaded particle was dissolved ($t_1$ to $t_2$) followed by the erosion of a BSA-488 loaded particle ($t_2$ to $t_3$) without disrupting neighboring particles. (b) Photodegradable particles can also be encapsulated within three-dimensional hydrogels and selectively photodegraded with focused light from an LSM ($\lambda$=405 nm). Here, BSA-488 loaded particles were encapsulated within fibrin hydrogels and eroded with focused LSM irradiation after the image t=0 s was taken. Images were captured after erosion to monitor diffusion of the protein through the fibrin gel. (c) Profiles of the diffusing protein were quantified over the time course of imaging and demonstrate that the BSA-488 diffused radially at a detectable level to a distance of 50 µm from the edge of the original particle. (d) Multiple protein loaded particle populations were encapsulated within a single fibrin gel and individual particles were eroded selectively as was demonstrated in 2D. Scale bars, 100 µm.

The microsphere formulation includes PEGdiPDA (poly (ethylene glycol)di-photodegradable-acrylate)[11] to render photodegradable, protein-loaded microspheres, on account of the o-nitrobenzyl ether moieties in the PEGdiPDA structure. Nitrobenzyl ethers (NBEs) undergo an irreversible cleavage upon irradiation, causing the network to degrade in response to specific wavelengths of light (FIG. 9.1). Similar macromers have been employed to form photoactive monolithic materials for applications ranging from cell culture[12-15] to drug delivery.[16-19] However, none of these approaches have combined microsphere processing techniques with the ability to deliver bioactive proteins to cells during culture with full spatiotemporal control.

The photodegradable microspheres described herein degrade upon single photon or multiphoton irradiation, which induces swelling and, ultimately, complete erosion and particle dissolution. During swelling, the entrapped protein diffuses into the surrounding environment and upon dissolution the total payload is released. In this system, the experimenter retains full control over the spatial and temporal presentation of the protein release by directing the irradiation. We demonstrate that biologically relevant proteins, namely TGF-αβ1 and Annexin V, can be entrapped within the microspheres and released on demand to direct or detect cell function. In total, we describe an innovative method to generate pre-loaded depots of protein agents, which can be employed to release bioactive proteins in the presence of cells.

Materials and Methods

Microsphere Preparation

Poly (ethylene glycol)di-photodegradable-acrylate (PEGdiPDA; $M_n \sim 4{,}070$ Da) was synthesized as previously described.[11,12] Poly (ethylene glycol)tetrathiol (PEG4SH; $M_n \sim 5{,}000$ Da) was synthesized as previously described.[20] Photodegradable microparticles were prepared via inverse suspension polymerization, in which PEGdiPDA was copolymerized with PEG4SH via base-catalyzed Michael addition in an aqueous phase that was suspended in an organic phase. Briefly, the organic phase was comprised of 5 ml of hexane containing 150 mg of a 3:1 ratio by weight of sorbitan monooleate (Span 80, Sigma-Aldrich) and poly (ethylene glycol)-sorbitan monooleate (Tween 80, Sigma-Aldrich).[21] The volume of the aqueous phase was 0.25 mL comprised of 300 mM triethanolamine (Sigma-Aldrich) at pH 8.0 with 6.2 wt % of PEGdiPDA, 3.8 wt % PEG4SH, and protein. Bovine serum albumin labeled with Alexa Fluor 488 or Alexa Fluor 594 (BSA-488 or BSA-594; Invitrogen) were entrapped at 0.8 mg/ml, TGF-β1 (Peprotech) was entrapped at 0.4 µg/ml, and the fluorescently labeled Annexin-V (Invitrogen) was entrapped at 20 v/v % Annexin-V conjugate solution. All of the components of the aqueous phase except for the PEG4SH solution were combined in a 1.7 ml microcentrifuge tube while the organic phase was added to a 20 ml scintillation vial with a stir bar. To initiate polymerization, the PEG4SH was added to the aqueous phase, which was subsequently vortexed for 10 s and quickly added to the organic phase. Mixing on a stir plate formed and maintained the inverse suspension between the two phases and the polymerization was allowed to proceed overnight.

Upon completion of the polymerization, the suspension was centrifuged (Eppendorf Centrifuge Model 5702) at 1000 rcf for 10 minutes and the supernatant was decanted. The microparticles were washed twice with hexanes and recovered with the same centrifugation conditions and once in 2-propanol and centrifuged at 2000 rcf for 10 minutes. The particles were then suspended in 1×PBS and washed three times by centrifuging (Eppendorf Centrifuge Model 5418) at 16,873 rcf for 15 minutes. The recovered particles were stored in PBS at 4° C. and a portion was imaged on a low vacuum scanning electron microscope (LVSEM, JSM-6480LV).

Absorbance of PEGdiPDA

The molar absorptivity of the nitrobenzyl ether (NBE) moiety was calculated by measuring the absorbance of solutions of NBE in a water:DMSO (80:20 v/v) blend at concentrations of 110, 82.5, 55, and 27.5 µM. The absorbance was measured on a UV-visible spectrophotometer (NanoDrop Spectrophotometer ND-1000) for each solution and the molar absorptivity was calculated from these absorbance profiles.

Microsphere Characterization with Image Analysis

Microparticles loaded with BSA-488 were used to characterize the size distribution of the particles. Particles were suspended in PBS and sealed between a glass slide and a cover slip in a rubber gasket, and imaged on an epifluorescent microscope (Nikon Eclipse TE2000-S). ImageJ (NIH) was used to threshold the images and the Analyze Particles plug-in was employed to determine the diameter of each microsphere. A total of 3130 particles were analyzed to determine the particle diameter distribution.

Degradation of Microspheres

BSA-488 loaded microparticles were suspended in PBS in a sealed rubber gasket and exposed to 365 nm ($I_0 = 13.5 \pm 0.5$ mW/cm$^2$; EXFO Omnicure 1000) or 400-500 nm ($I_0$=20.0±0.5 mW/cm$^2$; EXFO Novacure) irradiation to induce degradation and erosion. To quantify the degradation induced changes in material properties, a time series of images was captured with an epifluorescent microscope. The images were analyzed with ImageJ by bounding each particle with a manually drawn circle to determine the particle diameter at each timepoint during irradiation. The diameters were used to calculate the ratio of the actual volume relative to the initial volume (V/V$_0$) as a function of time for each particle, and data for the respective irradiation condition was plotted as an average of three particles.

To demonstrate focused irradiation induced degradation and erosion, BSA-488 and BSA-594 loaded microparticles were suspended in PBS in a sealed rubber gasket and placed on the stage of an overhead confocal laser-scanning microscope (Zeiss 710 NLO LSM). Particles were exposed to 405 nm (single photon; P=1 mW) or 740 nm (two-photon; P=100 mW) irradiation to degrade and, ultimately, erode the particles. Degradation and erosion were monitored by direct imaging on the LSM.

Quantification of BSA-488 Release

To quantify the release profile of entrapped BSA-488 from the particles, BSA-488 loaded microspheres were exposed to flood irradiation (λ=400-500 nm; $I_0$=20.0±0.5 mW/cm$^2$) for 0 min to 15 min. Samples were collected at each time point and centrifuged to separate the soluble protein in the supernatant from intact particles in solution. The fluorescence of the supernatant was measured on a plate reader (BioTek Synergy H1 Hybrid Reader) to determine the relative amount of BSA-488 in the supernatant for each sample.

Diffusion in Fibrin Gels

Fibrin gels were formed by combining 50 µl of fibrin (20 mg/ml), 1 µl of thrombin (0.5 U/ml), and 150 µl PBS with BSA-488 and BSA-594 loaded particles (2 mg of particles/ml). The solution was allowed to gel at 37° C. for 10 minutes in a sealed rubber gasket. The gels, with encapsulated particles, were imaged while the particles were degraded using an LSM (Zeiss 710 NLO LSM). Fluorescence intensity of the diffusing BSA-488 was quantified using the Image Processing Toolbox in MATLAB (MathWorks).

Cell Culture

All cell culture reagents were purchased from Invitrogen except where otherwise noted. PE25 cells, a cell line that produces luciferase in response to TGF-β1 exposure in a dose-dependent manner[22] were cultured in low glucose DMEM supplemented with 10% FBS, 1% penicillin/streptomycin, and 0.2% fungizone. PE25 cells were passaged every 2-3 days and maintained at less than 80% confluency. Passage 4-6 PE25 cells were used for TGF-β1 bioactivity assays. 3T3 fibroblasts were cultured in high glucose DMEM supplemented with 10% FBS, 1% penicillin/streptomycin, and 0.2% fungizone. 3T3 cells were passaged every 2-3 days and maintained at less than 70% confluency. P5 3T3 cells were used for the apoptosis assays.

TGF-β1 Delivery

For the TGF-β1 bioactivity assays, PE25 cells were plated on 24-well culture plates at 80,000 cells/well and allowed to adhere overnight. The following day, media with soluble TGF-β1 (2 ng/ml), media with TGF-β1 loaded particles (10 mg of particles/ml of media, which equates to 4 ng/ml TGF-β1 with complete release of the protein), media with blank particles (10 mg of protein-free particles/ml of media), and media were placed on the plated cells. Half of the wells were irradiated to degrade the particles (λ=365 nm; $I_0$=13.5±0.5 mW/cm$^2$) for 5 minutes to ensure complete erosion, while a duplicate set of conditions was not exposed to light. The solutions were left on the PE25 cells in an incubator for 16 hours. The following day, 200 µl of Glo-Lysis Buffer (Promega) was added to each well to lyse the cells and release any luciferase that had been produced. After 15 minutes, 50 µl of the lysis solution was combined with 50 µl of luciferin substrate in triplicate. The solutions were immediately quantified for luminescense on a plate reader (BioTek Synergy H1 Hybrid Reader).

Fluorescently Labeled Annexin V Delivery

Particles were synthesized that were loaded with AlexaFluor-594 Annexin V (Invitrogen) at 5 µl of Annexin V solution per 250 µl of particle solution. 3T3 cells were plated on a 6-well plate at 100,000 cells/well and allowed to adhere overnight. The following day, half of the wells were treated with (+)camptothecin (Sigma) at 10 M for 6 hours to induce apoptosis. After the treatment, the media was removed and substituted with 400 µl of Annexin V binding buffer (10 mM HEPES, 140 mM NaCl, 2.5 mM CaCl2 at a pH 7.4) containing soluble Annexin V (3 µl per 400 µl buffer) or Annexin V loaded particles (12.5 mg of particles/ml). A set of wells with Annexin V loaded particles was irradiated to release Annexin V (λ=365 nm; $I_0$=13.5±0.5 mW/cm$^2$) for 5 minutes. After 15 minutes, the samples were imaged on an LSM (Zeiss 710 LSM NLO).

Results and Discussion

Synthesis and Characterization of Microspheres

Figure 7:
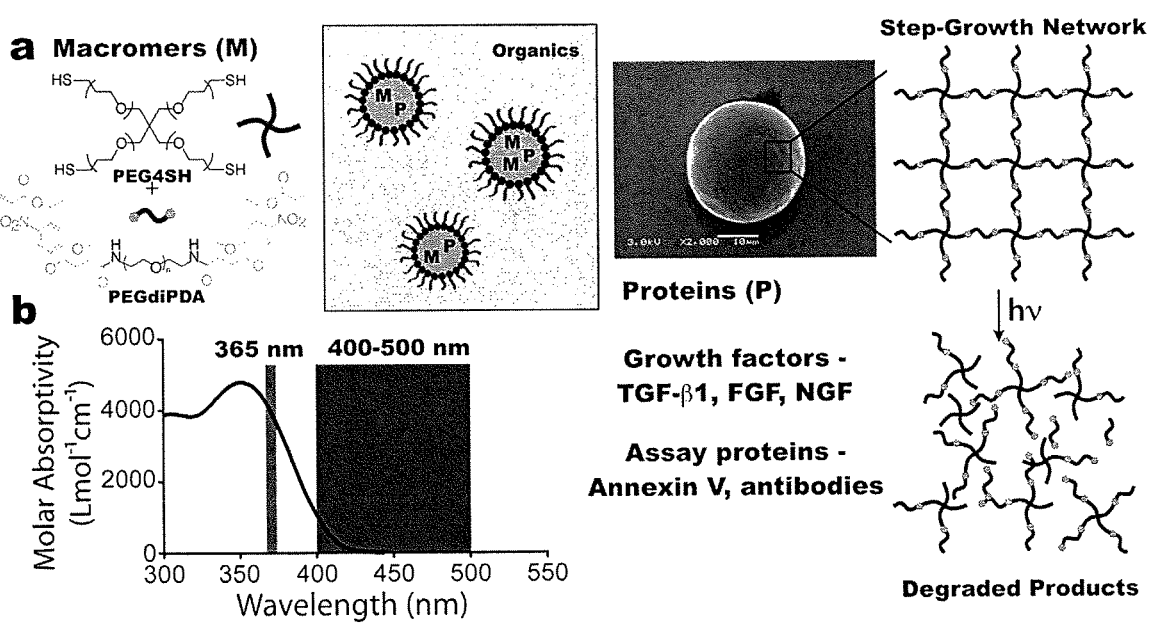
FIG. 7 shows photodegradable microparticle fabrication. (a) Photodegradable particles were synthesized by reacting PEG4SH with PEGdiPDA via base-catalyzed Michael addition in an inverse-phase, suspension polymerization. The aqueous phase, consisting of macromers, the base catalyst triethanolamine, and the target protein, was suspended in an organic phase of hexanes and stabilized by surfactants. Upon completion of the polymerization, the particles were purified via centrifugation resulting in spherical particles, as imaged by SEM. The reaction of the PEG4SH with the PEGdiPDA forms a step-growth network, and owing to the presence of nitrobenzyl ether (NBE) moieties in the PEGdiPDA, the network degrades in response to light. (b) The NBE moiety absorbs light strongly at 365 nm with a tail out past 405 nm. This allows both single photon irradiation at 365 nm or 400-500 nm to be used to degrade the particles, as well as two-photon irradiation using a wavelength of 740 nm.

Photodegradable microparticles were fabricated by reacting PEGdiPDA (Mn~4,000 Da) with poly(ethylene glycol) tetrathiol (PEG4SH; Mn~5,000 Da) via base-catalyzed Michael addition in an inverse-phase, microsuspension polymerization (FIG. 7a). The polymerization was carried out with the protein of interest included in the aqueous, macromer solution, which was suspended in an organic phase of hexanes with surfactants.[21] This approach allowed the target protein to be entrapped within the particles upon gelation. Subsequently, the particles were purified via centrifugation, resulting in smooth, protein-loaded hydrogel microspheres (FIG. 7a).

Figure 8:
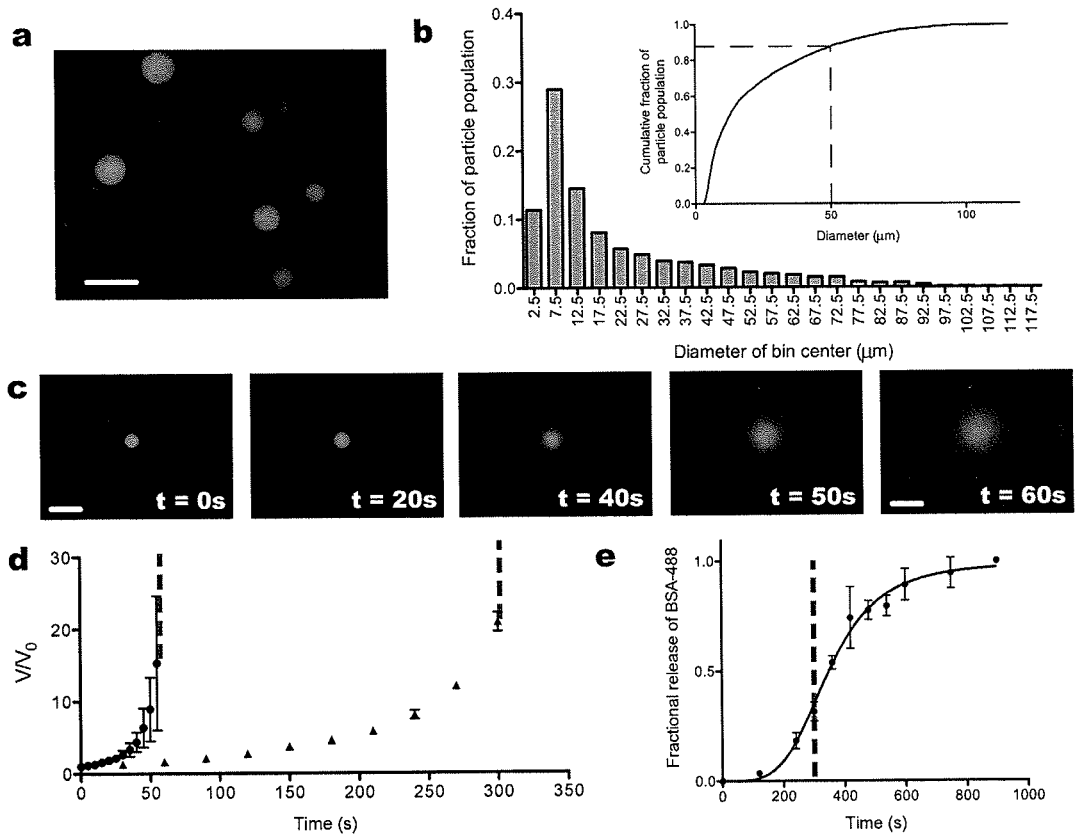
FIG. 8 shows size and degradation characteristics of photodegradable microparticles. (a) BSA-488 was entrapped within photodegradable microspheres. (b) Image analysis was used to quantify the size distribution of the particles synthesized by this method (n=3130). The particles were formed with a number average diameter of 22 µm and a diameter average diameter of 42 µm, which resulted in a polydispersity index of 1.9. Over 80% of the particles had a diameter less than 50 µm. (c) Photodegradable particles swell and, ultimately, erode in response to flood irradiation ($\lambda$=365 nm; $I_0$=13.5±0.5 mW/cm$^2$) over the time course of a minute. (d) The swelling was quantified with image analysis and plotted as normalized volume (V/V$_0$) as a function of irradiation time. Particles were exposed to 365 nm ($I_0$=13.5±0.5 mW/cm$^2$; circles) and 400-500 nm ($I_0$=20.0±0.5 mW/cm$^2$; triangles) irradiation, and the particles eroded at 55±5 s and 300±30 s for the two conditions, respectively (indicated by the dashed gray lines). (e) The release of BSA-488 as a function of irradiation time was quantified as the particles swelled and dissolved. Prior to dissolution (indicated by the dashed gray line), BSA-488 began diffusing out as the particles swelled, and after dissolution the majority of the payload was released into solution. Scale bars, 100 µm.

As a representative protein, fluorescently labeled bovine serum albumin (BSA-488) was incorporated into the macromer solution (FIG. 8a) during polymerization and entrapped homogeneously within the microsphere network. BSA-488 loaded particles were employed to characterize the size distribution of the particles via image analysis (n=3130 particles). The microspheres were synthesized with diameters on the order of 10 µm or greater, and more than 80% of the particles had a diameter less than 50 µm (FIG. 8b, inset). The distribution had a first moment ($D_n$)=22 µm, a second moment ($D_w$)=42 µm, and a polydispersity index (PDI)=1.9 (FIG. 8b). This size distribution is appropriate for the delivery of a substantial local dose of protein with rapid light-triggered degradation.

Photodegradation of Microspheres

Since the o-nitrobenzyl ether (NBE) moiety in the PEG-diPDA macromer is susceptible to cleavage with single photon or multiphoton excitation,[23,24] a broad range of irradiation conditions can be used to erode the microspheres and release the entrapped payload on the order of milliseconds to minutes. This process works as the NBE moieties in the PEGdiPDA structure introduce a photolabile linker into the network backbone of the microspheres. NBE moieties absorb light strongly in the UV (peak at 365 nm) with a tail that extends into the visible (FIG. 7b) and may undergo an irreversible cleavage upon absorption of light at these wavelengths, as well as absorption of two-photon irradiation centered at 740 nm. When a NBE is cleaved, the corresponding bond in the particle backbone is also cleaved. This process, which will be referred to as degradation, induces swelling in the particle as bonds are cleaved in the microsphere and the crosslinking density is decreased. Eventually, when a sufficient fraction of the bonds have been cleaved, erosion (i.e., mass loss) occurs and at these later stages of degradation, the microsphere is no longer a network, but soluble branched polymers that dissolve. To demonstrate degradation and protein release in response to single photon irradiation, BSA-488 loaded microspheres were irradiated with collimated light ($\lambda$=365 nm or 400-500 nm). Particles swelled initially, as bonds were cleaved throughout the network, as quantified by the increase in $V/V_0$ with irradiation time (FIG. 8c,d). Ultimately, the microspheres eroded completely when a sufficient number of bonds in the network were cleaved ($p_c$=0.42; the critical fraction of bonds that need to be cleaved to dissolve the network as determined by the Flory-Stockmayer equation) (FIG. 8c,d). For 365 nm irradiation at an intensity of 13.5±0.5 mW/cm$^2$, the microspheres swelled prior to eroding into solution over the course of 55±5 s. Whereas 400-500 nm irradiation at an intensity of 20.0±0.5 mW/cm$^2$ induced swelling and erosion over the course of 300±30 s. The fractional release of entrapped BSA-488 from the microspheres followed the degradation-induced swelling profile at short times and for the first 30% of release, while the bulk of the payload was released after complete particle dissolution (FIG. 8e). In this manner, collimated irradiation provides the user with temporal control over protein release within a culture system.

Selective Release of Proteins

Oftentimes the release of multiple factors within a single culture system is desirable, as cells respond in vivo to combinations of factors. For example, opposing gradients of transcriptional repressors, Hunchback and Knirps, direct proper development in *Drosophila*.[25] Light responsive protein release affords the unique ability to deliver multiple factors selectively within a single system. To demonstrate this concept, photodegradable microspheres were loaded with BSA-594 (BSA labeled with Alexa Fluor 594) and combined with BSA-488 loaded particles. A mixture of BSA-488 and BSA-594 spheres were plated and imaged on a confocal LSM (FIG. 9.3a). Focused irradiation ($\lambda$=405 nm single photon or 740 nm multiphoton) was employed to erode individual particles in sequence to release each desired protein (FIG. 9a). Initially, t=$t_1$, the focused irradiation ($\lambda$=740 nm; P=100 mW) was used to selectively erode a BSA-594 loaded microsphere. At a subsequent point in time, t=$t_2$, focused irradiation was employed to selectively erode a microsphere containing a second entrapped protein, BSA-488. In this manner, different growth factors or cytokines could be delivered locally and in combination over short distances to specific locations during culture. This system should prove useful for studies aimed at the investigation of synergistic protein interactions or to elucidate how multiple and/or opposing gradients influence cell fate or function, such as chemotaxis or tissue morphogenesis.

Release of Proteins in 3D Culture Platforms

Figure 10:
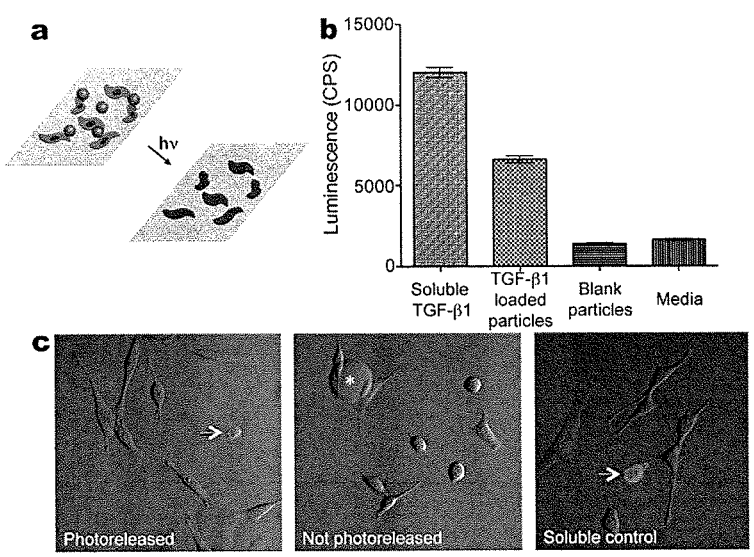
FIG. 10 shows release of bioactive proteins in the presence of cells. (a) Protein-loaded, photodegradable microparticles were incorporated into cell culture with plated cells. Collimated irradiation ($\lambda$=365 nm; $I_0$=13.5±0.5 mW/cm$^2$) was used to release the entrapped protein to direct or detect cell function. (b) TGF-β1 loaded particles were added to the media of plated PE25 cells, a TGF-β1 responsive reporter cell line, and compared to conditions: media with blank particles, media with soluble TGF-β1, and plain media. All samples were irradiated with the same dose used to erode particles and release the TGF-β1, and the response of the PE25 cells was compared between each condition. The TGF-β1 loaded particles had a significantly higher response than negative controls (blank particles and media alone), though not as strong a response as the positive control of soluble TGF-β1. This demonstrates that a significant fraction of the TGF-β1 remained bioactive upon entrapment and photorelease. (c) Fluorescently-labeled Annexin V loaded particles were added to the media on plated 3T3 cells. (+)Camptothecin was used to induce apoptosis and selected samples were irradiated to release the Annexin V. The samples were imaged to visualize cells labeled as apoptotic. Samples exposed to soluble Annexin V and photoreleased Annexin V stained positively for apoptosis (indicated by arrows at regions of red staining on the cell membranes), while there was no staining in the sample that was exposed to particles that were not photoreleased (particles are still visible in this image, denoted by the asterix).

Advanced three-dimensional culture platforms are increasingly employed for the study of cell biology and pathophysiology ex vivo.[26-28] Accompanying these advances is the need for methods to deliver proteins within these platforms in sophisticated manners, systematically introducing cues that recapitulate aspects of the native extracellular environment. Photoresponsive, pre-loaded depots of proteins were encapsulated within fibrin hydrogels (FIG. 9b,c) to demonstrate how this system might be used to deliver factors during 3D culture. Focused irradiation ($\lambda$=405 nm; P=1 mW) from a confocal LSM was used to dissolve individual particles, allowing the entrapped payload to release and diffuse through the gel (FIG. 9b). The released protein diffused, at a detectable level, ~50 μm radially from the edge of the particle (FIG. 9c). As was demonstrated in 2D, multiple proteins were released selectively within a single hydrogel to motivate combinatorial studies in 3D (FIG. 9d). In this manner, signaling proteins of interest can be delivered locally within a 3D cell culture scaffold. This light-controlled release and diffusion can be tailored to cell binding and uptake levels to influence cells and their function over reasonable length scales Release of Bioactive Proteins to Direct Cell Function The microsphere formulation was designed to accommodate a broad range of proteins including growth factors, cytokines, antibodies, and extracellular matrix components. To demonstrate that bioactive proteins can be incorporated and released from the photodegradable particles in the presence of cells, we entrapped a common and potent growth factor, TGF-β1,[29] within the microspheres. TGF-β1 loaded particles, as well as blank particles, were delivered to plated PE25 cells, a reporter cell line that produces luciferase in response to TGF-β1 exposure. The particles were dissolved with collimated irradiation ($\lambda$=365 nm, $I_0$=13.5±0.5 mW/cm$^2$) for 5 minutes to release the TGF-β1. PE25 cells that were exposed to TGF-β1 loaded particles significantly up-regulated luciferase production as compared to blank particles and media control (FIG. 10a). This demonstrates that the majority of the TGF-β1 remains bioactive upon entrapment and subsequent release. Furthermore, viability, as measured by a membrane integrity assay, was greater than 90% for all conditions (data not shown) indicating that the irradiation conditions and microsphere degradation products do not adversely affect cell function.

Release of Bioactive Proteins to Assay Cell Function

A further difficulty of in vitro culture is assaying a specific cell's functions during culture, and this can be especially challenging when culturing cells in 3D. To illustrate how photodegradable microspheres can be employed as protein loaded depots for assaying cell function, fluorescently conjugated Annexin V was loaded into microspheres. Annexin V loaded particles were delivered to plated NIH 3T3 fibroblasts, and the protein was photoreleased to identify apoptotic cells (FIG. 10c). Camptothecin was dosed to the cells prior to release to increase the rate of apoptosis in culture. Annexin V staining on the membranes of apoptotic cells was observed in the samples with photoreleased Annexin V and soluble Annexin V, whereas no membrane staining was observed in the sample in which the microspheres were not irradiated. To circumvent the challenge of assaying cell function during 3D culture, protein-loaded microspheres could be included in cell encapsulations so that the assay protein of interest can be delivered at a later time during culture.

Conclusion

The synthesis of photodegradable, PEG-based microspheres was demonstrated and these microspheres were employed to entrap and release soluble proteins. Cytocompatible irradiation conditions were determined to dissolve the particles with light, and the corresponding release of the entrapped payload was quantified during the degradation and erosion process. Multiple factors were loaded into batches of microspheres and focused irradiation was used to degrade individual particles selectively to release specific proteins of interest. TGF-β1 was loaded into the microspheres and was released with light to a reporter cell line to demonstrate that the entrapped and released protein remained bioactive. Similarly, Annexin V was loaded into particles to illustrate that protein-loaded depots could be incorporated into cell cultures to assay local cell function. By incorporating protein loaded, photoresponsive microspheres within cell aggregates, in media fed to plated cells, or in cell-laden scaffolds, the externally controlled and on-demand release of entrapped biological signals will allow experimenters to answer complex questions regarding the influence of sequential protein presentation on stem cell function or the response of cells to local gradients of chemokines or cytokines.

Example

This example includes predicted results which can be conducted based on description of this specification by those skilled in the art at the time of filing this application.

The method for making a photodegradable composition of the present invention, wherein the payload or biomolecule is a temperature sensitive payload entrapped as described herein. A benefit is the reduced temperature sensitivity of the payload. Examples of a temperature sensitive payloads include, but are not limited to, a vaccine, a protein, a folded protein, an enzyme, a hormone, anti-venom, an antibody, and an antibody fragment. A payload is temperature sensitive if exposure to temperatures outside of a prescribed range risks causing damage or irreversible change to the payload. One example of damage to a temperature sensitive payload involves a folded protein unfolding, or denaturing, at an elevated temperature. An benefit of entrapping a temperature sensitive payload in the photodegradable composition of the invention is to reduce the temperature sensitivity of the payload while entrapped within the photodegradable composition. In one embodiment, the present invention provides a method for making a photodegradable composition with a temperature sensitive payload entrapped therein, the method comprising: admix an aqueous phase of poly(ethylene glycol) di-photodegrable-acrylate (PEG-diPDA) with poly(ethylene glycol)tetrathiol (PEG4SH) and a temperature sensitive payload to form the aqueous phase; and dispense the aqueous phase onto a surface or into a mold of choice and allow a polymerization reaction to occur under controlled conditions.

When polymerized, the temperature sensitive payload entrapped within the photodegradable composition exhibits a reduction in sensitivity to temperature.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The definitions are provided to clarify their specific use in the context of the invention. All patents and publications mentioned in the specification are indicative of the levels of skill of those skilled in the art to which the invention pertains.

One skilled in the art would readily appreciate that the present invention is well adapted to carry out the objects and obtain the ends and advantages mentioned, as well as those inherent therein. The photodegradable compounds, macromers, and other components of the compounds, as well as the compounds and methods and accessory methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Although the description herein contains many specificities, these should not be construed as limiting the scope of the invention, but as merely providing illustrations of some of the embodiments of the invention. Thus, additional embodiments are within the scope of the invention and within the following claims. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

References

1. Dekanty, A. & Milan, M. The interplay between morphogens and tissue growth. *Embo Rep* 12, 1003-1010 (2011).
2. Leung, D. W., Cachianes, G., Kuang, W. J., Goeddel, D. V. & Ferrara, N. Vascular endothelial growth factor is a secreted angiogenic mitogen. *Science* 246, 1306-1309 (1989).
3. Plouet, J., Schilling, J. & Gospodarowicz, D. Isolation and Characterization of a Newly Identified Endothelial-Cell Mitogen Produced by Att-20 Cells. *Embo J* 8, 3801-3806 (1989).
4. Engler, A. J. et al. Embryonic cardiomyocytes beat best on a matrix with heart-like elasticity: scar-like rigidity inhibits beating. *J Cell Sci* 121, 3794-3802 (2008).
5. Freiberg, S. & Zhu, X. X. Polymer microspheres for controlled drug release. *Int J Pharm* 282, 1-18 (2004).
6. Peppas, N. A., Bures, P., Leobandung, W. & Ichikawa, H. Hydrogels in pharmaceutical formulations. *Eur J Pharm Biopharm* 50, 27-46 (2000).
7. Timko, B. P. et al. Advances in Drug Delivery. *Annu Rev Mater Res* 41, 1-20 (2011).
8. Berkland, C., King, M., Cox, A., Kim, K. & Pack, D. W. Precise control of PLG microsphere size provides enhanced control of drug release rate. *J Control Release* 82, 137-147 (2002).
9. Carpenedo, R. L. et al. Homogeneous and organized differentiation within embryoid bodies induced by microsphere-mediated delivery of small molecules. *Biomaterials* 30, 2507-2515 (2009).
10. Saito, N. et al. A biodegradable polymer as a cytokine delivery system for inducing bone formation. *Nat Biotechnol* 19, 332-335 (2001).

11. Kloxin, A. M., Tibbitt, M. W. & Anseth, K. S. Synthesis of photodegradable hydrogels as dynamically tunable cell culture platforms. *Nat Protoc* 5, 1867-1887 (2010).
12. Kloxin, A. M., Kasko, A. M., Salinas, C. N. & Anseth, K. S. Photodegradable hydrogels for dynamic tuning of physical and chemical properties. *Science* 324, 59-63 (2009).
13. Kloxin, A. M., Tibbitt, M. W., Kasko, A. M., Fairbairn, J. A. & Anseth, K. S. Tunable Hydrogels for External Manipulation of Cellular Microenvironments through Controlled Photodegradation. *Adv Mater* 22, 61-66 (2010).
14. Kloxin, A. M., Benton, J. A. & Anseth, K. S. In situ elasticity modulation with dynamic substrates to direct cell phenotype. *Biomaterials* 31, 1-8 (2010).
15. Tibbitt, M. W., Kloxin, A. M., Dyamenahalli, K. U. & Anseth, K. S. Controlled two-photon photodegradation of PEG hydrogels to study and manipulate subcellular interactions on soft materials. *Soft Matter* 6, 5100-5108 (2010).
16. Katz, J. S. et al. Modular synthesis of biodegradable diblock copolymers for designing functional polymersomes. *J Am Chem Soc* 132, 3654-3655 (2010).
17. Yesilyurt, V., Ramireddy, R. & Thayumanavan, S. Photoregulated release of noncovalent guests from dendritic amphiphilic nanocontainers. *Angew Chem Int Ed Engl* 50, 3038-3042 (2011).
18. Klinger, D. & Landfester, K. Photo-sensitive PMMA microgels: light-triggered swelling and degradation. *Soft Matter* 7, 1426-1440 (2011).
19. Peng, K. et al. Dextran based photodegradable hydrogels formed via a Michael addition. *Soft Matter* 7, 4881-4887 (2011).
20. Fairbanks, B. D., Singh, S. P., Bowman, C. N. & Anseth, K. S. Photodegradable, Photoadaptable Hydrogels via Radical-Mediated Disulfide Fragmentation Reaction. *Macromolecules* 44, 2444-2450 (2011).
21. Murthy, N. et al. A macromolecular delivery vehicle for protein-based vaccines: acid-degradable protein-loaded microgels. *P Natl Acad Sci Usa* 100, 4995-5000 (2003).
22. Clarke, D. C., Brown, M. L., Erickson, R. A., Shi, Y. & Liu, X. Transforming growth factor beta depletion is the primary determinant of Smad signaling kinetics. *Mol. Cell. Biol.* 29, 2443-2455 (2009).
23. Zhao, Y. et al. New caged coumarin fluorophores with extraordinary uncaging cross sections suitable for biological imaging applications. *J Am Chem Soc* 126, 4653-4663 (2004).
24. Aujard, I. et al. o-Nitrobenzyl photolabile protecting groups with red-shifted absorption: Syntheses and uncaging cross-sections for one- and two-photon excitation. *Chem-Eur J* 12, 6865-6879 (2006).
25. Clyde, D. E. et al. A self-organizing system of repressor gradients establishes segmental complexity in *Drosophila*. *Nature* 426, 849-853 (2003).
26. Abbott, A. Cell culture: biology's new dimension. *Nature* 424, 870-872 (2003).
27. Lutolf, M. P. & Hubbell, J. A. Synthetic biomaterials as instructive extracellular microenvironments for morphogenesis in tissue engineering. *Nat Biotechnol* 23, 47-55 (2005).
28. Tibbitt, M. W. & Anseth, K. S. Hydrogels as Extracellular Matrix Mimics for 3D Cell Culture. *Biotechnol Bioeng* 103, 655-663 (2009).
29. Shi, Y. & Massague, J. Mechanisms of TGF-beta signaling from cell membrane to the nucleus. *Cell* 113, 685-700 (2003).

What is claimed is:

1. A photodegradable composition comprising one or more macromers comprising a photodegradable group having the formula:

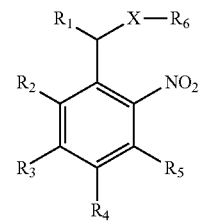

wherein said photodegradable group comprises; a) a polymeric backbone, and b) a polymerizable reactive end group;
where X is O, N or S;
$R_1$ is selected from the group consisting of: hydrogen, straight-chain or branched $C_1$-$C_{10}$ alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;
one of $R_2$, $R_3$, $R_4$, $R_5$ and $R_6$ is a backbone structure comprising one or more repeating units: poly(ethylene glycol), poly(ethylene oxide), poly(vinyl alcohol), poly(vinylpyrrolidone), poly(styrene), poly(acrylate), poly(methacrylates), poly(vinylethers), poly(urethane)s, polypropylene, polyester and polyethylene —O—$CH_2$—$CH_2C(O)NH$—$(CH_2CH_2O)_n$—C(O)—NH—$CH_2$—$CH_2$—O—, wherein n is 1-100;
$R_2$, $R_3$, $R_4$, $R_5$ and $R_6$ are each independently selected from the group consisting of: hydrogen; one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups of $R_1$, $R_2$, $R_3$, $R_4$, $R_5$ and $R_6$ can be linked to form one or more rings which can contain one or more of the same or different heteroatoms;
one or more R groups of $R_1$, $R_2$, $R_3$, $R_4$, $R_5$ and $R_6$ can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO-R'; —N(R')$_2$; —CO—N(R')$_2$; —NR'-CO—OR'; —SR'; —SOR'; —$SO_2$-R'; —$SO_3$R'; —$SO_2$N(R$^1$)$_2$; —P(R')$_2$; —$OPO_3$(R')$_2$; and —Si(R')$_3$, wherein each R', independent of other R' in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or -NH group; an optionally substituted aromatic group, two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups;

wherein at least one of $R_2$, $R_3$, $R_4$, $R_5$ and $R_6$ comprises a reactive end group, which is polymerizable.

2. The photodegradable composition of claim 1, wherein one of the others of $R_2$, $R_3$, $R_4$, $R_5$ and $R_6$ is a backbone structure comprising one or more repeating units; and the others of $R_2$, $R_3$, $R_4$, $R_5$ and $R_6$ are each independently selected from the group consisting of: hydrogen; one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure.

3. The photodegradable composition of claim 1, wherein the photodegradable group has the structure:

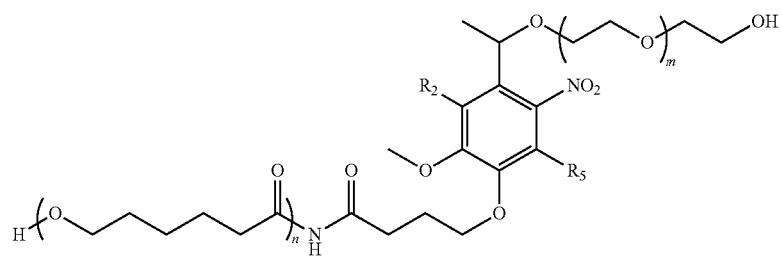

wherein m is an integer from 1-100; and
wherein n is an integer from 1-100;
one of $R_2$ and $R_5$ is a backbone structure comprising one or more repeating units: poly(ethylene glycol), poly(ethylene oxide), poly(vinyl alcohol), poly(vinylpyrrolidone), poly(styrene), poly(acrylate), poly(methacrylates), poly(vinylethers), poly(urethane)s, polypropylene, polyester and polyethylene, —O—$CH_2$—$CH_2C(O)NH$—($CH_2CH_2O)_n$—C(O)—NH—$CH_2$—$CH_2$—O—, wherein n is 1-100;
one of $R_2$ and $R_5$ are each independently selected from the group consisting of: hydrogen; one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups of $R_1$, $R_2$, $R_3$, $R_4$, $R_5$ and $R_6$ can be linked to form one or more rings which can contain one or more of the same or different heteroatoms;

one or more R groups of $R_2$ and $R_5$ can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO-R'; —N(R')$_2$; —CO—N(R')$_2$; —NR'-CO—OR'; —SR'; —SOR'; —$SO_2$-R'; —$SO_3$R'; —$SO_2$N(R$^1$)$_2$; —P(R')$_2$; —$OPO_3$(R')$_2$; and —Si(R')$_3$, wherein each R', independent of other R' in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or —NH group; an optionally substituted aromatic group, two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups;

wherein at least one of $R_2$ and $R_5$ comprises a reactive end group, which is polymerizable.

4. The photodegradable composition of claim 1, wherein the photodegradable group has the structure:

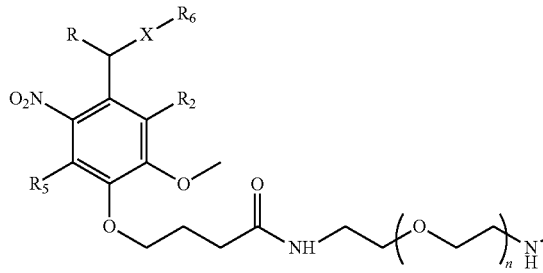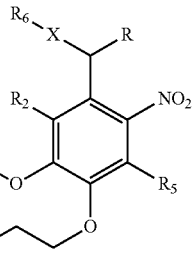

wherein n is an integer from 1-1000;
$R_1$ is selected from the group consisting of: hydrogen, straight-chain or branched $C_1$-$C_{10}$ alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;
one of $R_2$, $R_5$ and $R_6$ is a backbone structure comprising one or more repeating units: poly(ethylene glycol), poly(ethylene oxide), poly(vinyl alcohol), poly(vinylpyrrolidone), poly(styrene), poly(acrylate), poly(methacrylates), poly(vinylethers), poly(urethane)s, polypropylene, polyester and polyethylene, —O—$CH_2$—$CH_2$C(O)NH—($CH_2C_2$O)$_n$—C(O)—NH—$CH_2$—$CH_2$—O—, wherein n is 1-100;
one of $R_2$, $R_5$ and $R_6$ are each independently selected from the group consisting of: hydrogen; one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups of $R_1$, $R_2$, $R_3$, $R_4$, $R_5$ and $R_6$ can be linked to form one or more rings which can contain one or more of the same or different heteroatoms;
one or more R groups of $R_1$, $R_2$, $R_5$ and $R_6$ can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO-R'; —N(R')$_2$; —CO—N(R')$_2$; —NR'-CO—OR'; —SR'; —SOR'; —$SO_2$-R'; —$SO_3$R'; —$SO_2$N(R$^1$)$_2$; —P(R)$_2$; —$OPO_3$(R')$_2$; and —Si(R')$_3$, wherein each R', independent of other R' in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or —NH group; an optionally substituted aromatic group, two or more R' groups can be linked together to form a ring which may contain one or more of the same or different heteroatoms; and
R' can in turn be optionally substituted with one or more groups selected from the group consisting of halogens, nitro groups; cyano groups; isocyano groups; thiocyano groups; isothiocyano groups; azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups;
wherein at least one of $R_2$, $R_5$ and $R_6$ comprises a reactive end group, which is polymerizable.

5. The photodegradable composition of claim 1, wherein the photodegradable group has the structure:

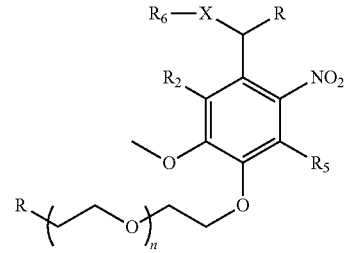

wherein n is an integer from 1-100;
$R_1$ is selected from the group consisting of: hydrogen, straight-chain or branched $C_1$-$C_{10}$ alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;
one of $R_2$, $R_4$, $R_5$ and $R_6$ is a backbone structure comprising one or more repeating units: poly(ethylene glycol), poly(ethylene oxide), poly(vinyl alcohol), poly(vinylpyrrolidone), poly(styrene), poly(acrylate), poly(methacrylates), poly(vinylethers), poly(urethane)s, polypropylene polyester and polyethylene, —O—$CH_2$—$CH_2$C(O)NH—($CH_2CH_2$O)$_n$—C(O)—NH—$CH_2$—$CH_2$—O—, wherein n is 1-100;
one of $R_2$, $R_4$, $R_5$ and $R_6$ are each independently selected from the group consisting of: hydrogen; one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or CH$_2$ moiety can be replaced with an oxygen atom, a nitrogen atom, an NR' group, or a S atom; and an optionally substituted aromatic or non-aromatic ring structure, wherein two or more R groups of R$_1$, R$_2$, R$_3$, R$_4$, R$_5$ and R$_6$ can be linked to form one or more rings which can contain one or more of the same or different heteroatoms;

one or more R groups of R$_1$, R$_2$, R$_4$, R$_5$ and R$_6$ can be optionally substituted with one or more substituent groups selected from halogens; nitro groups; cyano groups; isocyano groups; thiocyano groups; isothiocyano groups; azide groups; —SO$_2$ groups; —OSO$_3$H groups; one or more optionally substituted straight-chain, branched or cyclic alkyl, alkenyl or alkynyl groups; OR'; —CO—OR'; —O—CO-R'; —N(R')$_2$; —CO—N(R')$_2$; —NR'-CO—OR';—SR'; —SOR'; —SO$_2$-R'; —SO$_3$R'; —SO$_2$N(R$^1$)$_2$; —P(R')$_2$; —OPO$_3$(R')$_2$; and —Si(R')$_3$, wherein each R, independent of other R' in the substituent group can be a hydrogen, an optionally substituted straight-chain, branched or cyclic alkyl, alkenyl or alkynyl group wherein one or more C, CH or CH$_2$ groups therein can be replaced with an O atom, N atom, S atom or —NH group; an optionally substituted aromatic group, two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —SO$_2$ groups; —OSO$_3$H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups;

wherein at least one of R$_2$, R$_4$, R$_5$ and R$_6$ comprises a reactive end group, which is polymerizable.

6. The photodegradable composition of claim 1, wherein X-R$_6$ is a member of the group consisting of:

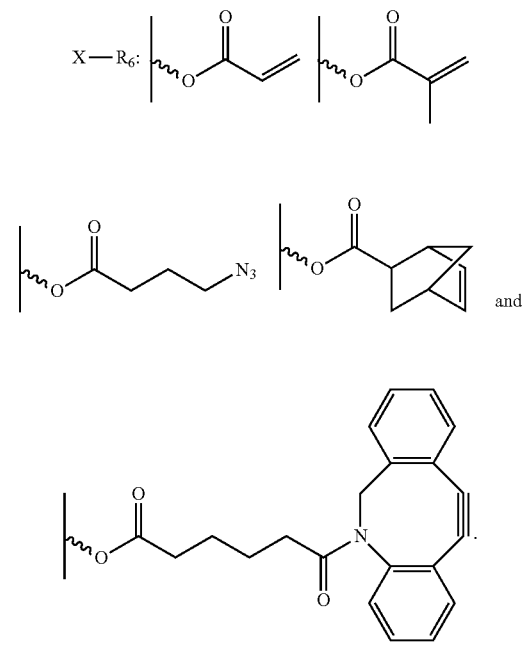

7. The photodegradable composition of claim 1, wherein the photodegradable group is poly(ethylene glycol) di-photodegradable-acrylate (PEG-diPDA) of the formula:

8. The photodegradable composition of claim 7, wherein the photodegradable group is reacted with poly(ethylene glycol) tetrathiol (PEG4SH).

9. The photodegradable composition of claim 1, wherein the composition forms a step-growth network.

10. The photodegradable composition of claim 1, wherein the composition forms a member selected from the group consisting of a microparticle, a nanoparticle, and a thin film.

11. The photodegradable composition of claim 1, wherein the polymerized composition has an entrapped biomolecule, which is releasable upon photodegradation of the composition.

12. The photodegradable composition of claim 11, wherein the composition is photodegraded with light irradiation at 200 nm to 500 nm.

13. The photodegradable composition of claim 12, wherein the composition is photodegraded with light irradiation at 365 nm or 400-500 nm.

14. The photodegradable composition of claim 11, wherein the composition is photodegraded with light irradiation at 390 nm to 850 nm.

15. The photodegradable composition of claim 14, wherein the composition is photodegraded with light irradiation at 740 nm.

16. The photodegradable composition of claim 1, wherein the entrapped biomolecule is a member selected from the group consisting of a protein, a peptide, an enzyme, an enzyme substrate, a vaccine, a hormone, an antibody, an antibody fragment, an antigen, a hapten, an avidin, a streptavidin, a carbohydrate, an oligosaccharide, a polysaccharide, a nucleic acid, a fragment of DNA, a fragment of RNA and a biological therapeutic.

17. The photodegradable composition of claim 16, wherein the entrapped biomolecule is a vaccine.

18. The photodegradable composition of claim 17, wherein the vaccine is a vaccine against a viral disease or a bacterial disease.

19. The photodegradable composition of claim 18, wherein the viral caused disease is selected from the group consisting of rabies, Hepatitis A, Hepatitis B, cervical cancer, genital warts, anogenital cancers, influenza, Japanese encephalitis, measles, mumps, rubella, poliomyelitis, rotaviral gastroenteritis, smallpox, chickenpox, shingles, and Yellow fever.

20. The photodegradable composition of claim 18, wherein the bacteria caused disease is selected from the group consisting of Anthrax, Whooping cough, Tetanus, Diphtheria, Q fever, Epiglottitis, meningitis, pneumonia, Tuberculosis, Meningococcal meningitis, Typhoid, fever, Pneumococcal pneumonia and Cholera.

21. A method for making a composition, the method comprising: copolymerizing one or more macromers comprising a) a photodegradable group having the formula:

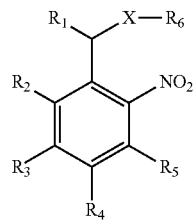

wherein said photodegradable group comprises; a) a polymeric backbone, and b) a polymerizable reactive end group;
where X is O, N or S;
$R_1$ is selected from the group consisting of: hydrogen, straight-chain or branched $C_1$-$C_{10}$ alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;
one of $R_2$, $R_3$, $R_4$, $R_5$ and $R_6$ is a backbone structure comprising one or more repeating units: poly(ethylene glycol), poly(ethylene oxide), poly(vinyl alcohol), poly(vinylpyrrolidone), poly(styrene), poly(acrylate), poly(methacrylates), poly(vinylethers), poly(urethane)s, polypropylene, polyester and polyethylene;
$R_2$, $R_3$, $R_4$, $R_5$ and $R_6$ are each independently selected from the group consisting of: hydrogen; one or more reactive end groups; straight chain, branched or cyclic $C_1$-$C_{20}$ alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups of $R_2$, $R_3$, $R_4$, $R_5$ and $R_6$ can be linked to form one or more rings which can contain one or more of the same or different heteroatoms;
one or more R groups of $R_1$, $R_2$, $R_3$, $R_4$, $R_5$ and $R_6$ can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO-R'; —N(R')$_2$; —CO—N(R')$_2$; —NR'-CO—OR'; —SR'; —SOR'; —$SO_2$-R'; —$SO_3$R'; —$SO_2$N(R$^1$)$_2$; —P(R')$_2$; —OPO$_3$(R')$_2$; and —Si(R')$_3$, wherein each R', independent of other R' in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or -NH group; an optionally substituted aromatic group, two or more R' groups can be linked together to form a ring which may contain one or more of the same or different heteroatoms; and
R' can in turn be optionally substituted with one or more groups selected from the group consisting of halogens, nitro groups; cyano groups; isocyano groups; thiocyano groups; isothiocyano groups; azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups;
wherein at least one of $R_2$, $R_3$, $R_4$, $R_5$ and $R_6$ comprises a reactive end group, with a member selected from the group consisting of a monomer, a macromer or other reactive compound.

22. The method for making a composition of claim 21, wherein the composition is selected from the group consisting of a microparticle, a nanoparticle, and a thin film.

23. The method for making a composition of claim 21, wherein the method comprises admixing an aqueous phase of poly(ethylene glycol) di-photodegrable-acrylate (PEG-diPDA) with poly(ethylene glycol) tetrathiol (PEG4SH) and a biomolecule to form the aqueous phase; and adding the aqueous phase to an organic phase to generate an inverse suspension polymerization reaction and form the photodegradable composition with a biomolecule entrapped therein.

24. The method for making a composition of claim 21, wherein the PEGdiPDA is copolymerized with PEG4SH via base-catalyzed Michael addition.

25. The method for making a composition of claim 21, wherein polymerization is initiated when PEG4SH is added to the aqueous phase, which is subsequently vortexed and added to the organic phase.

26. The method for making a composition of claim 21, wherein the organic phase comprises a hexane containing solution of sorbitan monooleate and poly (ethylene glycol)-sorbitan monooleate.

27. The method for making a composition of claim 21, wherein the entrapped biomolecule is a vaccine.

28. The method for making a composition of claim 27, wherein the vaccine is a vaccine against a viral disease or a bacterial disease.

29. The method for making a composition of claim 28, wherein the viral caused disease is selected from the group consisting of rabies, Hepatitis A, Hepatitis B, cervical cancer, genital warts, anogenital cancers, influenza, Japanese encephalitis, measles, mumps, rubella, poliomyelitis, rotaviral gastroenteritis, smallpox, chickenpox, shingles, and Yellow fever.

30. The method for making a composition of claim 28, wherein the bacteria caused disease is selected from the group consisting of Anthrax, Whooping cough, Tetanus, Diphtheria, Q fever, Epiglottitis, meningitis, pneumonia, Tuberculosis, Meningococcal meningitis, Typhoid, fever, Pneumococcal pneumonia and Cholera.

* * * * *